(12) United States Patent
Bonnal et al.

(10) Patent No.: US 9,314,604 B2
(45) Date of Patent: Apr. 19, 2016

(54) APPARATUS FOR SELECTIVELY ESTABLISHING A NEEDLELESS INJECTION PORT ON IV TUBING, AND ASSOCIATED METHODS

(75) Inventors: Olivier Bonnal, Melsungen (DE); Juergen Fuchs, Bad Emstal (DE); Andreas Katerkamp, Melsungen (DE); Christian Clobes, Alheim (DE); Mario Ebert, Felsberg (DE)

(73) Assignee: B. Braun Melsungen AG, Melsungen (DE)

( * ) Notice: Subject to any disclaimer, the term of this patent is extended or adjusted under 35 U.S.C. 154(b) by 1019 days.

(21) Appl. No.: 13/377,484

(22) PCT Filed: Jul. 15, 2010

(86) PCT No.: PCT/US2010/042196
§ 371 (c)(1),
(2), (4) Date: Feb. 6, 2012

(87) PCT Pub. No.: WO2011/009004
PCT Pub. Date: Jan. 20, 2011

(65) Prior Publication Data
US 2012/0130305 A1 May 24, 2012

Related U.S. Application Data

(60) Provisional application No. 61/226,204, filed on Jul. 16, 2009.

(51) Int. Cl.
*A61M 39/02* (2006.01)
*A61M 39/12* (2006.01)
(Continued)

(52) U.S. Cl.
CPC ............... *A61M 39/02* (2013.01); *A61M 39/12* (2013.01); *A61M 39/14* (2013.01); *A61M 39/26* (2013.01); *A61M 2039/087* (2013.01); *Y10T 137/0402* (2015.04)

(58) Field of Classification Search
CPC ..................... A61M 39/04; A61M 2039/1072; A61M 39/26; A61M 2039/1027; A61M 2039/262; A61M 2039/263; A61M 2039/267; A61M 39/02; A61M 39/045; A61M 39/10; A61M 2039/1077; A61M 2039/266
USPC ........ 604/256, 533, 537, 167.01, 167.03, 323
See application file for complete search history.

(56) References Cited

U.S. PATENT DOCUMENTS 4,998,927 A * 3/1991 Vaillancourt ................. 604/537
5,230,706 A 7/1993 Duquette
(Continued)

OTHER PUBLICATIONS

International Search Report completed Mar. 28, 2011 and mailed Mar. 29, 2011from corresponding International Application No. PCT/US2010/042196 filed Jul. 15, 2010 (3 pages).

(Continued)

*Primary Examiner* — Bradley Osinski
(74) *Attorney, Agent, or Firm* — Klein, O'Neill & Singh, LLP

(57) ABSTRACT

Apparatus enables one or more needleless injection ports to be established on IV tubing as needed. An IV tubing-engaging portion secures the apparatus about the tubing. A puncturing member establishes fluid communication between the IV line and a sealing member on the apparatus. Connecting a syringe to the sealing member establishes fluid communication between the IV line and the syringe, enabling an injection to be made. When the syringe is withdrawn, the sealing member reseals to prevent fluid leakage from the IV line.

12 Claims, 28 Drawing Sheets

(51) Int. Cl.
*A61M 39/26* (2006.01)
*A61M 39/14* (2006.01)
*A61M 39/08* (2006.01)

(56) References Cited

U.S. PATENT DOCUMENTS 6,524,304 B1 2/2003 Picou et al.
6,635,044 B2 * 10/2003 Lopez .......................... 604/500
6,648,835 B1 * 11/2003 Shemesh ....................... 600/573
2006/0111694 A1 5/2006 Fukai et al.
2008/0262465 A1 10/2008 Zinger

OTHER PUBLICATIONS

Written Opinion completed Mar. 28, 2011 and mailed Mar. 29, 2011from corresponding International Application No. PCT/US2010/042196 filed Jul. 15, 2010 (4 pages).

* cited by examiner

APPARATUS FOR SELECTIVELY ESTABLISHING A NEEDLELESS INJECTION PORT ON IV TUBING, AND ASSOCIATED METHODS

CROSS-REFERENCE TO RELATED APPLICATIONS

This application is a national phase application of International Application No. PCT/US2010/042196, filed Jul. 15, 2010, which claims the benefit of U.S. Provisional Application No. 61/226,204, filed Jul. 16, 2009, the contents of which are expressly incorporated herein by reference.

BACKGROUND

The embodiments discussed herein relate to needleless ports for injecting fluids into an IV line.

DESCRIPTION OF RELATED ART

When a patient is receiving intravenous (IV) fluids, it is sometimes necessary to also give the patient an injection of medicine. Since the patient already has an IV line connected, it is advantageous to give the injection through the IV line to avoid having to stick another needle into the patient. Several products on the market enable injections to be administered into the IV line so that the injected fluid can flow into the patient through the IV line. Such products provide a needleless injection port at a convenient point along the length of the IV line.

Unfortunately, known needleless injection ports are permanently integrated into IV tubing. They thus raise the cost of producing the tubing. The extra cost may be wasted if the port is ultimately never used.

SUMMARY

The various embodiments of the present apparatus for selectively establishing a needleless injection port on IV tubing, and associated methods, have several features, no single one of which is solely responsible for their desirable attributes. Without limiting the scope of the present embodiments as expressed by the claims that follow, their more prominent features now will be discussed briefly. After considering this discussion, and particularly after reading the section entitled "Detailed Description of the Preferred Embodiments," one will understand how the features of the present embodiments provide advantages, which include the capability to selectively establish one or more needleless injection ports at any point along an IV tube whenever desired.

One aspect of the present apparatus and methods includes the realization that existing products sometimes unnecessarily increase the cost of producing IV tubing. When an IV tube including a permanently integrated needleless injection port is used, the cost of using that IV tube is greater than the cost of using an IV tube that does not include a needleless injection port. If the port is never used, the extra cost is wasted. It would be advantageous to have the capability to selectively establish one or more needleless injection ports as desired, so that IV tubing can be produced without the added expense of integrating permanent needleless injection ports. Needleless injection ports would then seldom be wasted, because they could be established only when needed.

One embodiment of the present apparatus is configured to be secured to intravenous (IV) tubing to establish a needleless injection/aspiration port on the IV tubing. The apparatus comprises an IV tubing-engaging portion having an internal surface defining an internal bore configured to wrap around an external surface of the IV tubing. The apparatus further comprises a branch portion extending from the IV tubing-engaging portion. The branch portion includes a lumen. The apparatus further comprises a valve member comprising a body section having an inlet coupled to the branch portion. The valve member comprises a compressible piston having a hollow interior cavity disposed, at least in part, inside the body section for regulating fluid flow through the inlet of the body section. A puncturing member having a shaft and a sharp tip is disposed, at least in part, inside the hollow interior cavity of the compressible piston. The puncturing member is structured to move axially from a first position inside the hollow interior cavity of the compressible piston to a second position in which at least part of the puncturing member is moved inside the internal bore of the IV tubing-engaging portion.

Another embodiment of the present apparatus is configured to be secured to intravenous (IV) tubing to establish a needleless injection/aspiration port on the IV tubing. The apparatus comprises an IV tubing-engaging portion having an internal surface configured to snugly engage an external surface of the IV tubing. The apparatus further comprises a tubular branch portion extending from the IV tubing-engaging portion. The branch portion includes a lumen. The apparatus further comprises a first elastomeric sealing member located at a junction of the IV tubing-engaging portion and the branch portion. The sealing member fluidly isolates the lumen of the branch portion from an interior of the IV tubing-engaging portion. The apparatus further comprises a piston portion engaging the branch portion. A central shaft of the piston portion is disposed at least partially within the lumen of the branch portion. The central shaft includes a lumen. The apparatus further comprises a puncturing member extending distally from the central shaft and including a lumen and a pointed distal tip. The apparatus further comprises a valve member engaging a proximal end of the piston portion. The valve member includes a second elastomeric sealing member that provides selective sealing of a proximal end of the piston portion. Relative translation of the piston portion with respect to the branch portion in a first direction drives the pointed tip of the puncturing member through the first elastomeric sealing member and through a sidewall of the IV tubing to establish fluid communication between an interior of the IV tubing and the lumen in the puncturing member.

One embodiment of the present methods of securing apparatus to intravenous (IV) tubing to create a needleless injection/aspiration port on the IV tubing comprises positioning a first section of an IV tubing-engaging portion of the apparatus on the IV tubing. The method further comprises moving a second section of the IV tubing-engaging portion relative to the first section to at least partially surround a length of the IV tubing and to bring an internal surface of the IV tubing-engaging portion into snug engagement with an external surface of the IV tubing. The method further comprises engaging an injection apparatus with a valve member of the apparatus such that a male portion of the injection apparatus penetrates a slit in a first elastomeric sealing member of the valve member to open fluid communication through the valve member. The method further comprises translating the valve member and a piston portion to which the valve member is secured in a first direction relative to a tubular branch portion extending perpendicularly to the IV tubing-engaging portion. The method further comprises advancing the piston portion toward the IV tubing as the piston portion translates relative to the branch portion. The method further comprises advancing a puncturing member that extends distally from the piston portion toward the IV tubing as the piston portion advances toward the IV tubing. The method further comprises puncturing a second elastomeric sealing member located at a junction of the IV tubing-engaging portion and the branch portion with the puncturing member as it advances toward the IV tubing. The method further comprises puncturing the IV tubing with the puncturing member to establish fluid communication between an interior of the IV tubing and a lumen in the puncturing member.

BRIEF DESCRIPTION OF THE DRAWINGS

The various embodiments of the present apparatus for selectively establishing a needleless injection port on IV tubing, and associated methods, now will be discussed in detail with an emphasis on highlighting the advantageous features. These embodiments depict the novel and non-obvious apparatus shown in the accompanying drawings, which are for illustrative purposes only. These drawings include the following figures, in which like numerals indicate like parts.

DETAILED DESCRIPTION

Figure 1:
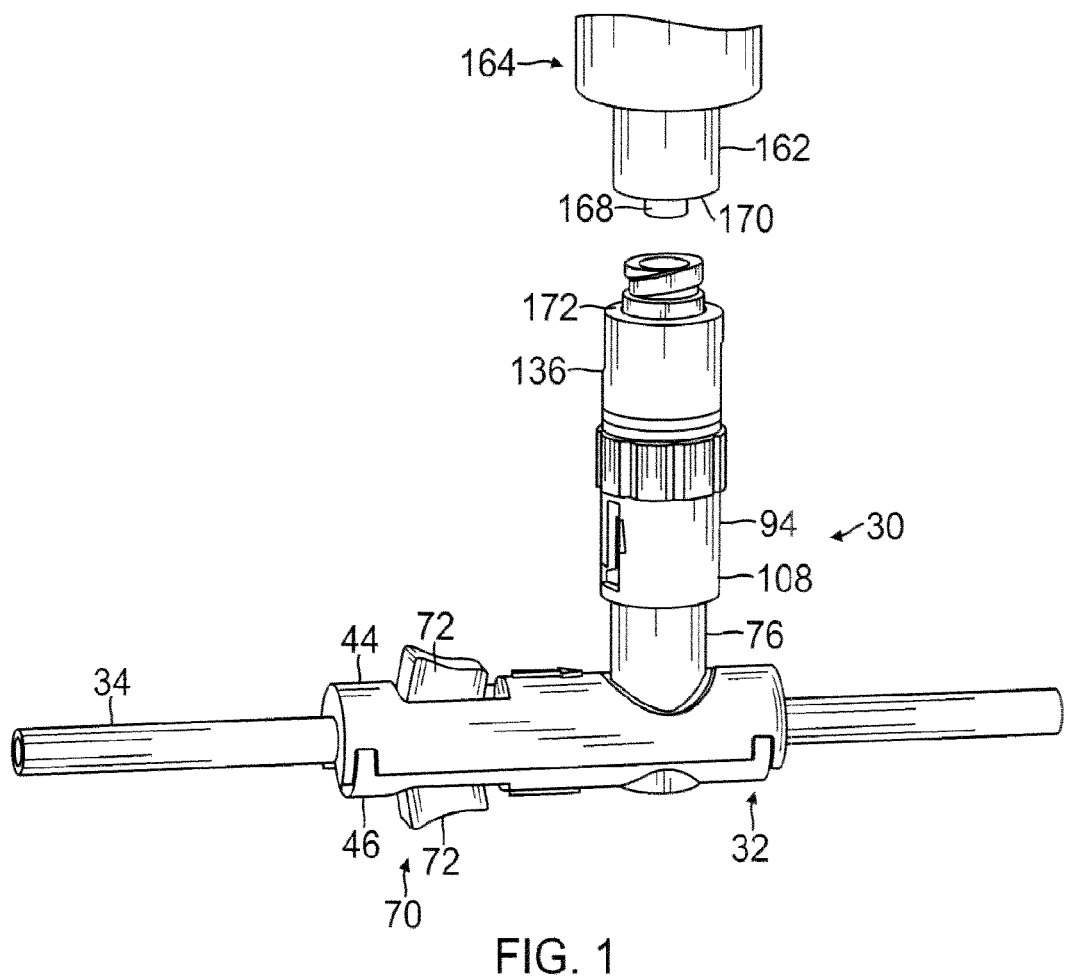
FIG. 1 is a front perspective view, of another embodiment of the present apparatus for selectively establishing a needleless injection port on IV tubing, illustrating the apparatus secured to IV tubing with an injection apparatus exploded from the injection port.

The following detailed description describes the present embodiments with reference to the drawings. In the drawings, reference numbers label elements of the present embodiments. These reference numbers are reproduced below in connection with the discussion of the corresponding drawing features.

As used herein, the term "proximal" describes a surface or portion of a component that is located nearer to the operator than other surfaces or portions of that component when the apparatus is in use. Similarly, the term "distal" describes a surface or portion of a component that is located farther from the operator than other surfaces or portions of that component when the apparatus is in use.

Figure 1A:
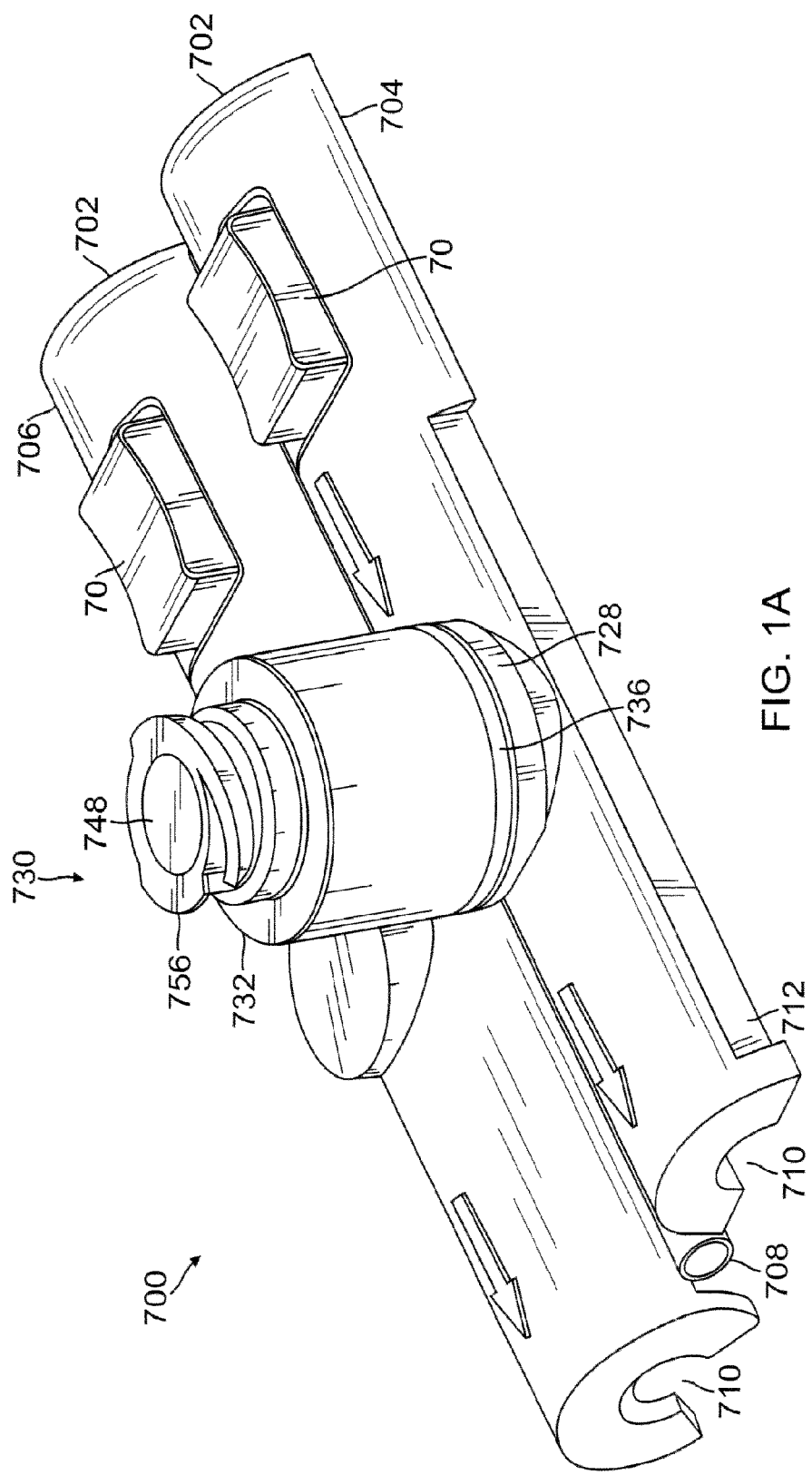
FIG. 1A is a front perspective view of one embodiment of the present apparatus for selectively establishing a needleless injection port on an IV tubing.
Figure 1B:
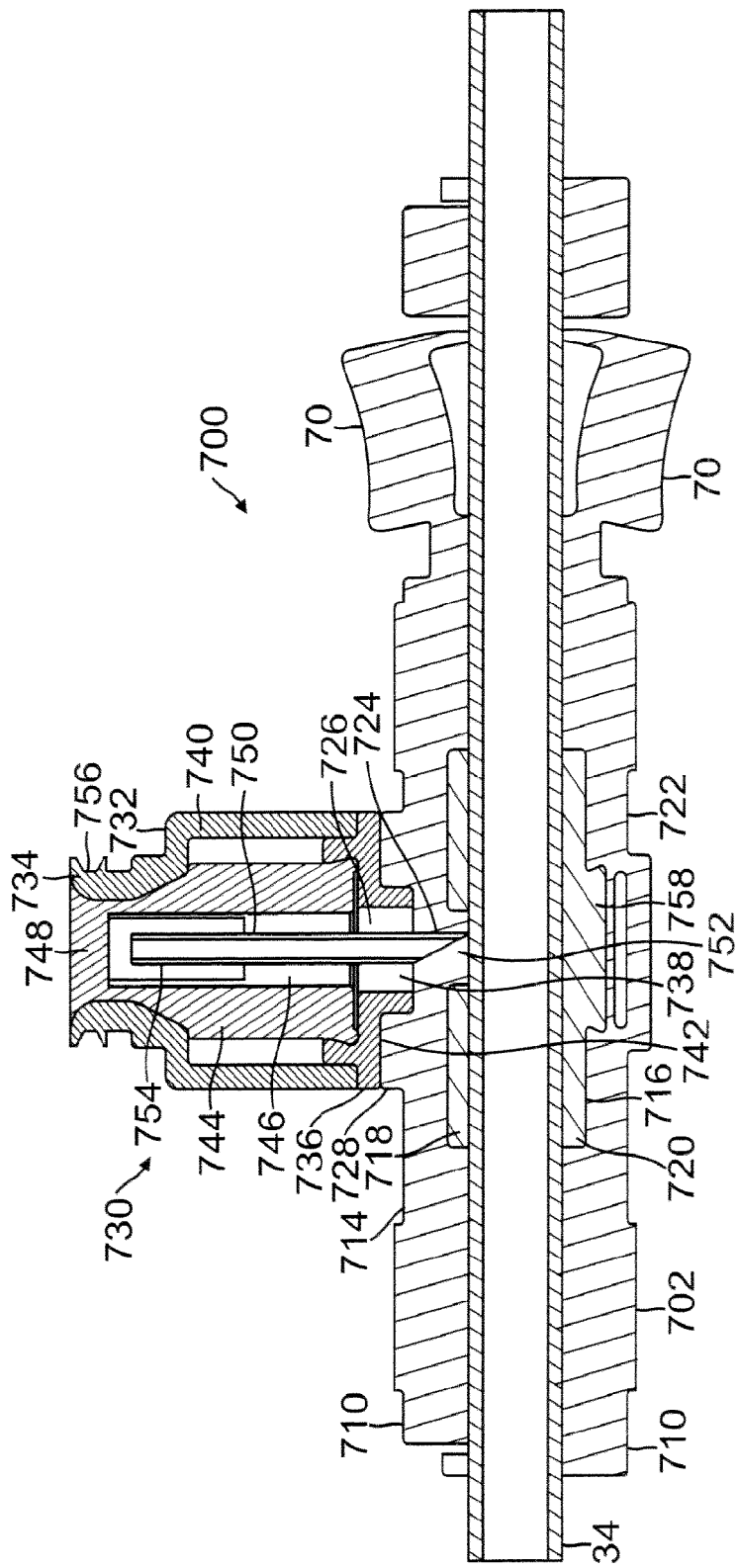
FIG. 1B is a front cross-sectional view of the apparatus of FIG. 1A, illustrating the apparatus secured to the IV tubing.

FIGS. 1A and 1B illustrate one embodiment of the present apparatus 700 for selectively establishing a needleless injection port on intravenous (IV) tubing 34. The apparatus 700 includes an IV tubing-engaging portion or saddle 702 configured to at least partially surround a portion of the IV tubing 34 to secure the apparatus 700 to the tubing 34. The tubing 34 is, or can be, connected to an IV supply source, such as a diluent or IV solution, and/or to a patient. With reference to FIG. 1A, the IV tubing-engaging portion 702 includes first and second sections 704, 706 secured to one another at a hinge 708. The first and second sections 704, 706 are each shaped substantially, at least along an outer periphery, as half cylinders.

FIG. 1A illustrates an open configuration, in which the first and second sections 704, 706 are freely pivotable with respect to one another about the hinge 708. In this configuration, the first section 704 can be positioned on the IV tubing 34 such that the tubing 34 resides in a recess 710 in the interior of the first section 704. In the illustrated embodiment, the recess 710 is shaped substantially as a half cylinder and is sized to snugly engage the exterior of the IV tubing 34. The second section 706 similarly includes a recess 710 shaped and sized to snugly engage the exterior of the IV tubing 34. From the open configuration shown in FIG. 2, the second section 706 can be pivoted about the hinge 708 to enclose a length of the tubing 34 within the recesses 710 of the two sections. FIG. 1B illustrates the closed configuration in which the IV tubing-engaging portion 702 surrounds a length of the tubing 34 and secures the apparatus 700 to the tubing 34.

In certain embodiments, the first and second sections 704, 706 may include a latch, a first portion 712 of which is shown in FIG. 1A. The latch retains the IV tubing-engaging portion 702 in the closed configuration to resist removal of the apparatus 700 from the tubing 34. The structure and function of latches are discussed in further detail below with respect to alternative embodiments of the present apparatus.

With reference to FIG. 1B, the recess 710 in the second section 706 includes a first diameter that is selected to enable the second section 706 to snugly engage the exterior of the IV tubing 34, which in one embodiment includes a slight compression fit. Along a portion of its length, however, the recess 710 includes a second, larger, diameter that forms a semi-cylindrical cavity 714. The first section 704 also includes a cavity 716 positioned opposite the first cavity 714. The second cavity 716 is also semi-cylindrical, but includes a disk-shaped portion 722 opposite the first cavity 714. Each cavity 714, 716 receives a semi-cylindrical elastomeric sealing member 718, 720. When the IV tubing-engaging portion 702 is in the closed position, the sealing members 718, 720 snugly engage a portion of the tubing 34, as shown in FIG. 1B. As discussed in detail below, the sealing members 718, 720 provide a seal at their interface with the tubing 34 so that liquid does not leak from around the site where the apparatus 700 punctures the tubing 34, which is also discussed in detail below. The sealing members 718, 720 may be constructed from silicone, for example, or any other suitable elastomeric material that is capable of providing a seal against IV tubing 34, such as a thermoplastic elastomer (TPE). In other embodiments, the first and second sections 704, 706 are sized and made with materials that seal against the IV tubing in the absence of a separate sealing member. In still other embodiments, a sealing member may be formed around the general area of the puncturing member only.

With continued reference to FIG. 1B, a post 724 extends from a floor of the cavity 714 toward the second section 706 of the IV tubing-engaging portion 702. A height of the post 724 is equal to a depth of the cavity 714. An aperture 726 extends through the post 724 and the first section 704, perpendicularly to a longitudinal axis of the IV tubing-engaging portion 702. About the aperture 726, the first section 704 includes a ring-shaped boss 728 on its outer surface, which may be referred to as a branch extending from the first section 704.

With reference to FIGS. A and 1B, the IV tubing-engaging portion 702 further includes an optional clamp 70 located in an upstream region of the IV tubing-engaging portion 702. The clamp 70 enables an operator to pinch the flexible tubing 34 and restrict fluid flow through the tubing 34. The structure and function of clamp 70 is discussed in further detail below with respect to alternative embodiments of the present apparatus.

With continued reference to FIGS. 1A and 1B, a valve member 730 extends perpendicularly from the first section 704 of the IV tubing-engaging portion 702. In other embodiments the valve member 730 may extend from the IV tubing-engaging portion 702 at a different angle than perpendicularly. With reference to FIG. 1B, the valve member 730 includes a substantially cylindrical housing 732 having a female Luer inlet 734 at its proximal end. A distal end of the housing 732 receives an adapter 736 that is shaped substantially as a disk having a central aperture 738. A proximal face of the adapter 736 includes a first ring-shaped boss 740 about the aperture 726, the boss 740 having a first diameter. A distal face of the adapter 736 includes a second ring-shaped boss 742 about the aperture 726, the boss 742 having a second diameter. The second diameter is smaller than the first diameter. The first ring-shaped boss 740 seats within the distal end of the housing 732, and the second ring-shaped boss 742 seats within the ring-shaped boss 728 on the outer surface of the first section 704 of the IV tubing-engaging portion 702.

The housing 732 contains an elastomeric sealing member 744 having a tubular lumen 746. The sealing member 744, also referred to as a piston or internal core, controls fluid flow through the inlet of the valve member 730. A proximal region 748 of the sealing member 744 fills the inlet 734, thereby sealing the inlet 734. The proximal region 748 includes a transverse slit (not shown) that is compressed on itself by the relative dimension of the housing 732. The compressed slit seals fluid from flowing through the lumen 746.

The lumen 746 in the sealing member 744 contains a puncturing or piercing member 750. The puncturing member 750 includes a lumen (not shown) and a pointed distal tip 752. The puncturing member lumen opens to the distal tip 752, which forms an angle of approximately 45° to a longitudinal axis of the puncturing member 750, similar to a standard hypodermic needle. A cylindrical sleeve or holding member 754 receives a proximal end of the puncturing member 750. An interior of the sleeve 754 engages the puncturing member 750, and an exterior of the sleeve 754 is held in the lumen 746 of the sealing member 744, just distal of the proximal region 748. The puncturing member 750 may be secured within the sleeve 754 with a friction fit, by welding, by adhesive, or by any other suitable means. Similarly, the sleeve 754 may be secured within the sealing member 744 with a friction fit, detent, slight compression, welding, adhesive, other suitable means or combinations thereof to permit movement to a second position, as further discussed below. In alternative embodiments, the sleeve 754 may be formed integrally with the puncturing member 750, or the sleeve 754 may be omitted and the puncturing member 750 may be secured directly to the sealing member 744.

The puncturing member 750 extends distally from the sleeve 754 through the lumen 746 in the sealing member 744. A distal region of the puncturing member 750 extends through the apertures 738, 726 in the adapter 736 and the first section 704 of the IV tubing-engaging portion 702. In certain embodiments, one or both of the apertures 726, 738 may have a diameter substantially equal to or slightly larger than an outside diameter of the puncturing member 750. The apertures 726, 738 are thus able to guide the puncturing member's 750 movement, which is described below.

The slit provides a path through the sealing member 744 for a male Luer connector at the distal end of an injection apparatus, such as a syringe (not shown). The male Luer connector is securable to the valve member 730 by engaging internal threads (not shown) on the shroud of the connector with the external threads 756 on the female Luer inlet 734 of the valve member 730. A process for connecting an injection apparatus, such as a syringe, to the valve member 730 is described below.

The apparatus 700 illustrated in FIGS. 1A and 1B advantageously creates an injection port at any desired location along a length of IV tubing. For example, an operator may take an existing length of IV line that is already in use and create a port for providing flow through the created port. To establish the port, the operator begins with the apparatus 700 in the open configuration of FIG. 1A. He or she then positions the first section 704 of the IV tubing-engaging portion 702 against the IV tubing 34 at the desired location. The first section 704 is positioned such that the tubing 34 rests in the recess 710 of the first section 704. The operator then pivots the second section 706 about the hinge 708 to move the IV tubing-engaging portion 702 to the closed position around the tubing 34, as shown in FIG. 1B. The latch retains the IV tubing-engaging portion 702 in the closed position, so that the apparatus 700 does not accidentally disengage the tubing 34.

The operator next engages an injection apparatus, such as a syringe (not shown), with the valve member 730. To do so, the operator engages the male Luer fitting at the distal end of the syringe with the female Luer inlet 734 at the proximal end of the valve member 730. The internal threads on the male Luer fitting engage the external threads 756 on the female Luer inlet 734 as the syringe is rotated in a first direction relative to the valve member 730. As the male connector is screwed onto the female connector 734, a nozzle or male tip at the distal end of the male connector pushes against the proximal region 748 of the sealing member 744 and compresses the sealing member 744. In one embodiment, the sealing member 744 buckles in random folds in response to the force of the male tip. Concurrently, the sleeve 754 and the puncturing member 750 are forced distally. In the configuration shown in FIG. 1B, the distal tip 752 of the puncturing member 750 is spaced from an outer surface of the IV tubing 34. However, as the sleeve 754 and the puncturing member 750 are forced distally the pointed distal tip 752 of the puncturing member 750 is forced through the IV tubing 34. Concurrently, the slit opens and fluid communication is established between the male Luer connector and the IV tubing 34 through the sealing member lumen 746.

When the injection apparatus has been secured to the valve member 730 as described above, the operator may depress a plunger on the injection apparatus to inject liquid medicament into the IV tubing 34 through the sleeve 754 and the puncturing member 750. In other embodiments, a hydrophobic filter (not shown) may be used to vent the lumen 746. During the injection, the operator may occlude liquid flow upstream from the puncturing member 750 by pinching the clamp 70. The process of occluding fluid flow using the clamp 70 is described in further detail below with respect to alternative embodiments.

When the puncturing member 750 pierces the IV tubing 34, liquid may flow out of the IV tubing 34 through a puncture created by the puncturing member 750. The sealing members 718, 720 and the proximal region 748 of the sealing member 744 resist leakage of this liquid from the apparatus 700. Like the sealing members 718, 720, the sealing member 744 may be constructed from silicone, for example, or any other suitable elastomeric material that is capable of providing a seal having a slit. Further, the second sealing member 720 includes a thickened portion 758 opposite the aperture 726. The thickened portion 758 provides a backstop for the distal tip 752 of the puncturing member 750. If the puncturing member 750 should pass entirely through the IV tubing 34, the thickened portion 758 receives the distal tip 752 and forms a seal around the puncture in the IV tubing 34.

After performing an injection, the male connector 162 may be withdrawn from the apparatus by twisting it in the direction opposite that used to advance the male connector 162 into the sealing member 744. As the male connector 162 is withdrawn, the sealing member 744 reverts to its original shape, forcing the proximal region 748 to fit into the inlet 734 of the valve member 730, which forces the walls of the slit to come together to reseal the proximal end 154 of the sealing member 136. As the sealing member 744 reverts to its original shape, it draws the sleeve 754 and the puncturing member 750 with it, returning them to the position shown in FIG. 1B. The puncturing member 750 is thus withdrawn from the IV tubing 34. Liquid may flow from within the IV tubing 34 through a puncture left by the puncturing member 750. The sealing members 718, 720 and the proximal region 748 of the sealing member 744 resist leakage of this liquid from the apparatus 700.

In another embodiment, as the sealing member 744 reverts to its original shape, it separates from the sleeve 754. In this embodiment, the force holding the puncturing member 750 in the pierced IV tubing 34 is greater than the force holding the sleeve 754 in the sealing member 744, which may be a simple friction fit. The puncturing member 750 thus remains pierced to and in fluid communication with the IV tubing 34 while the seal member returns to its original position. In other embodiments, the seal member does not include a transverse slit and instead forces fluid to flow around the outside of the seal member, in the space between the interior surface of the housing 732 and the outside exterior surface of the seal member. Provisions are made to then direct fluid flow through the piercing member, such by placing the inlet to the piercing member below the valve and creating flow channels to direct flow into the inlet of the piercing member.

Figure 2:
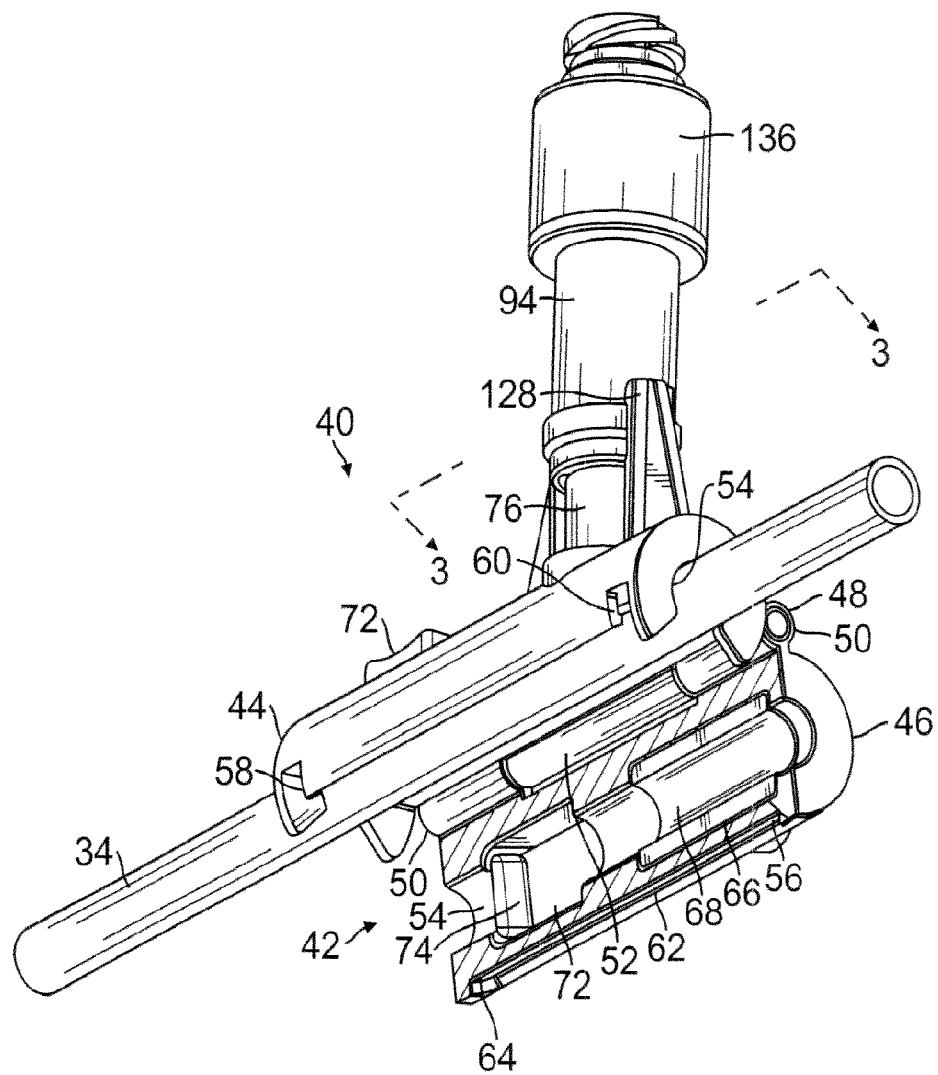
FIG. 2 is a bottom, right-side perspective view of another embodiment of the present apparatus for selectively establishing a needleless injection port on IV tubing, illustrating the apparatus engaging IV tubing.

FIG. 1 illustrates another embodiment of the present apparatus 30 for selectively establishing a needleless injection port on intravenous (IV) tubing 34. The apparatus 30 includes an IV tubing-engaging portion or saddle 32 configured to at least partially surround a portion of the IV tubing 34 to secure the apparatus 30 to the tubing 34. The tubing 34 is, or can be, connected to an IV supply source, such as a diluent or IV solution, and/or to a patient. With reference to FIG. 2, which illustrates another embodiment of the present apparatus 40, the IV tubing-engaging portion 42 includes first and second sections 44, 46 secured to one another at a hinge 48. The first and second sections 44, 46 are each shaped substantially, at least along an outer periphery, as half cylinders.

The hinge 48 comprises first cylindrical hinge parts 50 extending from an edge of the second section 46 and a second cylindrical hinge part 52 extending from an edge of the first section 44. The second hinge part 52 resides between the first hinge parts 50 and is rotatable relative to the first hinge parts 50. In certain embodiments a hinge pin (not shown) may extend through the hinge parts 50, 52 to rotatably secure them together. In certain other embodiments the hinge parts 50, 52 may include structural features, such as interconnected posts and recesses 54, that rotatably secure them together without or in addition to the hinge pin.

FIG. 2 illustrates an open configuration, in which the first and second sections 44, 46 are freely pivotable with respect to one another about the hinge 48. In this configuration, the first section 44 can be positioned on the IV tubing 34 such that the tubing 34 resides in a recess 54 in the interior of the first section 44. In the illustrated embodiment, the recess 54 is shaped substantially as a half cylinder and is sized to snugly engage the exterior of the IV tubing 34. The second section 46 similarly includes a recess 54 shaped and sized to snugly engage the exterior of the IV tubing 34. From the open configuration shown in FIG. 2, the second section 46 can be pivoted about the hinge 48 to enclose a length of the tubing 34 within the recesses 54 of the two sections. FIG. 1 illustrates the closed configuration in which the IV tubing-engaging portion 32 surrounds a length of the tubing 34 and secures the apparatus 30 to the tubing 34, similar to when the first and second sections 44, 46 of the saddle 42 of FIG. 2 are engaged with one another.

In certain embodiments, the first and second sections 44, 46 may include a latch 56 (FIG. 2) that retains the IV tubing-engaging portion 32 in the closed configuration to resist removal of the apparatus 30 from the tubing 34. In certain further embodiments, the latch 56 may be configured to resist opening so that the apparatus 30 cannot be removed from the tubing 34 without damaging the apparatus 30 and/or the tubing 34. In the embodiment of FIG. 2, a first latch part 58 comprises a cantilevered extension from the sidewall of the first section 44. An inner surface of the first latch part 58 includes an inwardly extending flange 60. The second section 46 includes a second latch part comprising a recess 62. The recess 62 is sized and shaped to receive the first latch part 58. The recess 54 includes a ramp 64 and a flange-receiving space located behind the ramp 64. When the second section is 46 moved toward the closed configuration, the flange 60 contacts the ramp 64, which increasingly bends the first latch part 58 outward as the flange 60 rides farther up the ramp 64. When the flange 60 passes over the top of the ramp 64, it snaps into the flange-receiving space behind the ramp 64. In the closed configuration, the flange 60 bears against a rear surface of the ramp 64, resisting movement of the first latch part 58 out of the recess 54, which in turn resists movement of the IV tubing-engaging portion 32 toward the open configuration.

Figure 3:
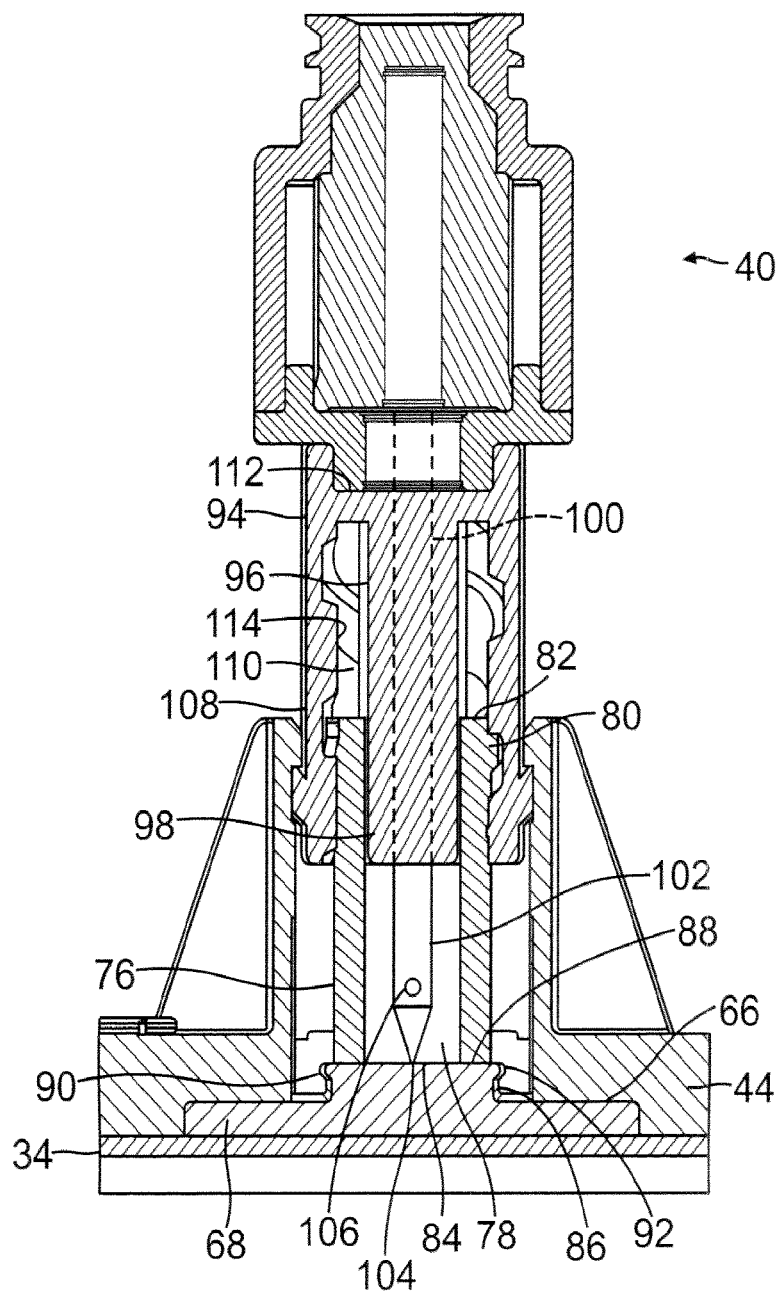
FIGS. 3 and 3A are a front cross-sectional view of the apparatus of FIG. 2 taken through the line 3-3 in FIG. 2.

With reference again to FIG. 2, the recess 54 in the second section 46 includes a first diameter that is selected to enable the second section 46 to snugly engage the exterior of the IV tubing 34, which in one embodiment includes a slight compression fit. Along a portion of its length, however, the recess 54 includes a second, larger, diameter that forms a semi-cylindrical cavity 66. With reference to FIG. 3, the first section 44 includes a semi-cylindrical cavity 66 that is a mirror image of the cavity 66 in the second section 46. Each cavity 66 receives a semi-cylindrical elastomeric sealing member 68. When the IV tubing-engaging portion 32 is in the closed position, the sealing members 68 snugly engage a portion of the tubing 34, as shown in FIG. 3. As discussed in detail below, the sealing members 68 provide a seal at their interface with the tubing 34 so that liquid does not leak from around the site where the apparatus 30, 40 punctures the tubing 34, which is also discussed in detail below. The sealing members 68 may be constructed from silicone, for example, or any other suitable elastomeric material that is capable of providing a seal against IV tubing 34, such as a thermoplastic elastomer (TPE).

With reference to FIG. 1, the IV tubing-engaging portion 32 further includes an optional clamp 70 located in an upstream region of the IV tubing-engaging portion 32. The clamp 70 comprises first and second push buttons 72 extending outward in opposite directions from the IV tubing-engaging portion 32. With reference to FIG. 2, each of the push buttons 72 is cantilevered to one of the first and second sections 44, 46. A clamp part 74 extends inwardly from the underside of each push button 72. When the IV tubing-engaging portion 32 is in the closed position (FIG. 1), the clamp parts 74 bear lightly against, or are spaced from, the tubing 34. When an operator squeezes the push buttons 72 toward one another, the clamp parts 74 move toward one another, pinching the flexible tubing 34 and restricting fluid flow through the tubing 34. If the operator applies sufficient force, he or she can completely occlude fluid flow.

As described in further detail below, the operator may occlude fluid flow at a location upstream from an injection site prior to giving the injection through the apparatus 30, 40.

Occluding fluid flow upstream from the injection site causes the injected fluid to flow to the patient, rather than upstream through the IV line. In certain embodiments, the clamp 70 may include a releasable latch (not shown) to temporarily lock the clamp parts 74 in an occluding position so that the operator does not have to hold the clamp 70 with one hand while giving an injection with the other hand.

With reference to FIG. 1, a tubular branch portion 76 extends perpendicularly from the IV tubing-engaging portion 32. In other embodiments the branch portion 76 may extend from the IV tubing-engaging portion 32 at a different angle than perpendicularly. With reference to FIG. 3, the branch portion 76 includes a lumen 78 and an external thread 80 at its proximal end 82. The sealing member 68 seals the distal end 84 of the lumen 78. A substantially disk-shaped protrusion 86 extends from the sealing member 68 toward the lumen 78. A proximal surface 88 of the protrusion 86 abuts the distal end 84 of the lumen 78, providing a seal. A flange 90 extends around the proximal edge of the protrusion 86. An annular recess 92 in the interior sidewall of the first section 44 receives the flange 90. Engagement of the flange 90 and the annular recess 92 retains the sealing member 68 within the recess 66 when the apparatus 30, 40 is in the open configuration (FIG. 2).

With reference to FIGS. 1-3, a piston portion 94 engages the branch portion 76. With reference to FIG. 3, the piston portion 94 includes a central shaft 96 having a distal region 98 disposed within the lumen 78 of the branch portion 76. A lumen 100 extends completely through the central shaft 96. A puncturing member 102 extends distally from the central shaft 96. The puncturing member 102 includes a lumen (not shown) and a pointed distal tip 104. The puncturing member 102 may extend at least partially through the lumen 100 in the central shaft 96. A distal region of the puncturing member 102 includes at least one opening 106. In the illustrated embodiment, the opening 106 is in a sidewall of the puncturing member 102. In alternative embodiments, the distal end of the puncturing member 102 may be open, as in a standard hypodermic needle.

With continued reference to FIG. 3, the piston portion 94 further includes a cylindrical outer wall 108 separated from the central shaft 96 by an annular space 110. A proximal end wall 112 connects the outer wall 108 and the central shaft 96. An inner surface of the outer wall 108 includes threads 114 that engage the external thread 80 on the branch portion 76. Due to the engagement of the threads 80, 114, rotation of the piston portion 94 in a first direction relative to the branch portion 76 advances the piston portion 94 distally, as explained in further detail below.

Figure 3A:
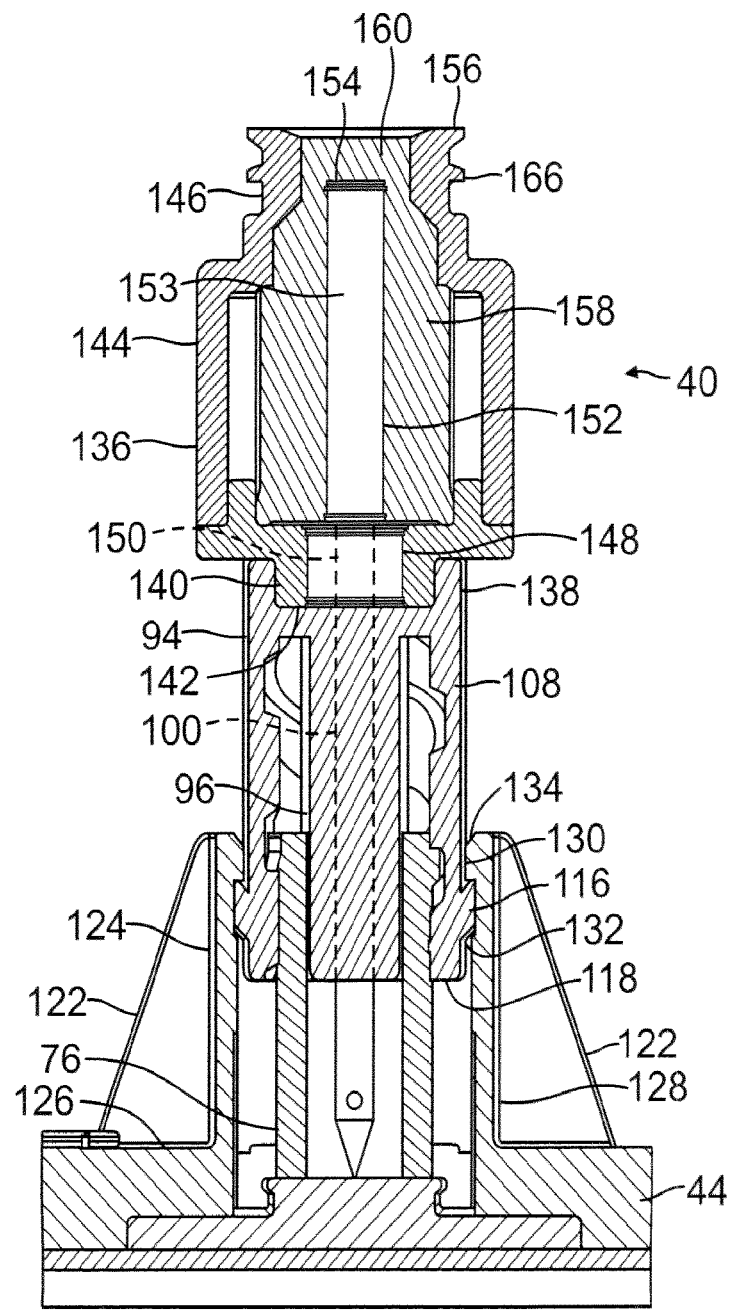

With reference to FIG. 3A, an exterior surface of the outer wall 108 includes an annular flange 116 near its distal end 118. The annular flange 116 resists accidental disengagement of the piston portion 94 from the branch portion 76, as described in further detail below.

With continued reference to FIG. 3A, the apparatus 30 further includes a stabilizer 121 for the piston portion 94. The stabilizer comprises first and second uprights 122 that extend outwardly from the first section 44 of the IV tubing-engaging portion 32 on opposite sides of the piston portion 94. Each of the uprights 122 is shaped substantially as a right triangle, with a long leg 124 extending along the piston portion 94 and a short leg 126 extending along the first section 44. With reference to FIGS. 2 and 3A, a transverse wall 128 extends perpendicularly outward in both directions from the plane defined by each upright 122 along the long leg 124. A flange 130 (FIG. 3A) extends toward the piston portion 94 at the proximal end of each upright 122. The uprights 122 help to stabilize the piston portion 94 by resisting side-to-side tilting of the piston portion 94 as it is rotated relative to the branch portion 76.

With continued reference to FIG. 3A, a spacing between the uprights 122 is substantially equal to an outer diameter of the annular flange 116 on the outer wall 108. A spacing between the flanges 130 on the uprights 122 is substantially equal to an outer diameter of the outer wall 108. The flanges 130 thus form a barrier that resists accidental disengagement of the piston portion 94 from the branch portion 76. A distal surface 132 of the annular flange 130 is oriented at an angle to the outer sidewall 108 of the piston portion 94. Similarly, a proximal surface 134 of each flange 130 is oriented at an angle to its respective transverse wall 128. The surfaces 132, 134 form ramps that engage one another and force the uprights 122 outward to enable the piston portion 94 to be screwed onto the branch portion 76. In one embodiment, the angles of the ramps 132, 134 are equal.

With continued reference to FIG. 3A, a valve member 136 engages a proximal end 138 of the piston portion 94. A nut 148 located at the distal end of the valve member 136 includes a central disk-shaped protrusion 140 that seats in a complementary recess 142 at the proximal end 138 of the piston portion 94. The valve member 136 further includes a generally cylindrical housing 144 attached to the nut 148. The housing 144 has a female Luer inlet 146 at its proximal end. The nut 148 includes a lumen 150 that adjoins a proximal end of the lumen 100 in the central shaft 96. In one embodiment, the nut 148 is a separate piece secured to the outer wall 108 of the piston 94. In another embodiment, the nut 148 and the outer wall of the piston 94 are a single integral piece.

The housing 144 contains an elastomeric sealing member 158 having a tubular lumen 152. The sealing member 158, also referred to as a piston or internal core, controls fluid flow through the valve member 136 and consequently through the shaft 96. A proximal region 160 of the sealing member 158 is sealed by the relative dimension of the inlet 146, which forces a transverse slit (not shown) in the sealing member 158 to compress on itself and seal fluid from flowing through the lumen 152.

The slit provides a path through the sealing member 158 for a male Luer connector 162 (FIG. 1) at the distal end of an injection apparatus, such as a syringe 164. The male Luer connector 162 is securable to the valve member 136 by engaging internal threads (not shown) on the shroud of the connector 162 with the external threads 166 on the female Luer connector 146 of the valve member 136. As the male connector 162 is screwed onto the female connector 146, a nozzle or male tip 168 (FIG. 1) at the distal end of the male connector 162 pushes against the proximal region of the sealing member 158 and compresses the sealing member. In one embodiment, the sealing member 158 buckles in random folds in response to the force of the male tip 168. Concurrently, the slit opens and fluid communication is established between the lumen 152 of the sealing member 158, the male Luer connector 162, the lumens 100, 150, and the lumen in the puncturing member 102. When the male connector 162 is withdrawn, the sealing member 158 reverts to its original shape, forcing the proximal region 160 to fit into the inlet 146 of the valve member 136, which forces the walls of the slit to come together to reseal the proximal end 154 of the sealing member 136. The sealing member 158 may be constructed from silicone, for example, or any other suitable elastomeric material that is capable of providing a seal having a slit.

The apparatus 30, 40 illustrated in FIGS. 1-3 advantageously creates an injection port at any desired location along a length of IV tubing. For example, an operator may take an existing length of IV line that is already in use and create a port for providing flow through the created port. To establish the port, the operator begins with the apparatus 30, 40 in the open configuration. He or she then positions the first section 44 of the IV tubing-engaging portion 32 against the IV tubing 34 at the desired location. The first section 44 is positioned such that the tubing 34 rests in the recess 54 of the first section 44, as shown in FIG. 2. The operator then pivots the second section 46 about the hinge 48 to move the IV tubing-engaging portion 32 to the closed position around the tubing 34, as shown in FIG. 1. The latch 56 retains the IV tubing-engaging portion 32 in the closed position, so that the apparatus 30 does not accidentally disengage the tubing 34.

The operator next engages an injection apparatus, such as a syringe 164, with the valve member 136. To do so, the operator engages the male Luer fitting 162 at the distal end of the syringe 164 with the female Luer fitting 146 at the proximal end 156 of the valve member 136. The internal threads on the male Luer fitting 162 engage the external threads 166 on the female Luer fitting 146 as the syringe 164 is rotated in a first direction relative to the valve member 136. The nozzle 168 on the male Luer fitting 162 advances against the proximal surface of the sealing member and opens the slit establishes fluid communication between the syringe 164 and the lumens 100, 150, 152 and the lumen in the puncturing member 102.

When the male Luer fitting 162 has been completely screwed into the valve member 136, a distal annular shoulder 170 on the shroud of the male Luer fitting 162 engages a proximal annular shoulder 172 on the female Luer fitting 164 (FIG. 1). Any further rotation of the syringe 164 in the first direction induces rotation of the valve member 136 and piston portion 94 relative to the branch portion 76. However, prior to advancing the piston portion 94 distally into the branch portion 76, the operator preferably purges air from the lumens 100, 150, 152 and the lumen in the puncturing member 102. The purging step may be performed several different ways, as described below with respect to various embodiments configured for various different purging methods.

After purging the air from the lumens 100, 150, 152 and the lumen in the puncturing member 102, the operator rotates the syringe 164, the valve member 136 and the piston portion 94 in the first direction relative to the branch portion 76 to advance the piston portion 94 distally with respect to the branch portion 76. The advancing piston portion 94 drives the pointed tip 104 (FIG. 3) of the puncturing member 102 through the elastomeric sealing member 68 and through a sidewall of the IV tubing 34 to establish fluid communication between an interior of the IV tubing 34 and the lumen in the puncturing member 102. The sealing member 68 seals around the puncturing member 102 and the opening in the tubing 34 to prevent liquid from leaking through the interface of the puncturing member 102 and the opening. With fluid communication established, the operator can inject liquid from the syringe 164 into the IV tubing 34 by depressing a plunger (not shown) on the syringe 164. To restrict the injected liquid from flowing upstream in the IV tubing 34, the operator can pinch the clamp 70 upstream from the injection site while depressing the plunger. In an alternative embodiment, the puncturing member 102 punctures the IV tubing by rotating the valve member 136 without having to first engage a syringe to the valve member.

After completing the injection, the operator simply rotates the syringe to separate it from the valve member 136. The valve member remains in the active position, in which the puncturing member 102 projects into the IV tubing 34. The sidewalls on either side of the slit come together after the syringe is removed to reseal the proximal end 154 of the tubular member 152. The port 30, 40 is then ready for reuse at any time by simply inserting the syringe into the inlet of the valve member to open the slit. Thus, one aspect of the present embodiments is an apparatus for selectively creating an access port along a length of IV tubing to enable fluid communication between the port and the IV tubing. In a particular embodiment, the fluid communication is created in a sidewall of the IV tubing by puncturing the wall of the IV tubing. As a specific example, the apparatus for forming a port along a length of IV tubing comprises a saddle having a bore for accommodating the tubing, a branch nozzle extending from the saddle comprises a lumen; a piston portion comprising a lumen engageable with the branch nozzle so that the two lumens communicate; and a valve member comprising a housing having an inlet port and a sealing member disposed therein; wherein a puncturing member is disposed with the piston member so that a shaft of the puncturing member is coaxial with the piston member; and wherein the puncturing member comprises a sharp distal tip for puncturing the IV tubing.

In an alternative embodiment (not shown), the IV tubing-engaging portion may not include first and second hinged sections. Instead, the IV tubing-engaging portion may comprise a single piece having a cylindrical longitudinal opening sized to snugly fit the tubing 34. This embodiment could be combined with IV tubing 34 during manufacture, or by a medical professional prior to establishing the IV line in the patient. The alternative apparatus could be moved along the IV line to any convenient location, and only used if needed. If unused, the alternative apparatus could later be removed from the IV line after it is removed from the patient so that the alternative apparatus could be used again with a different IV line in a later procedure.

Figure 4:
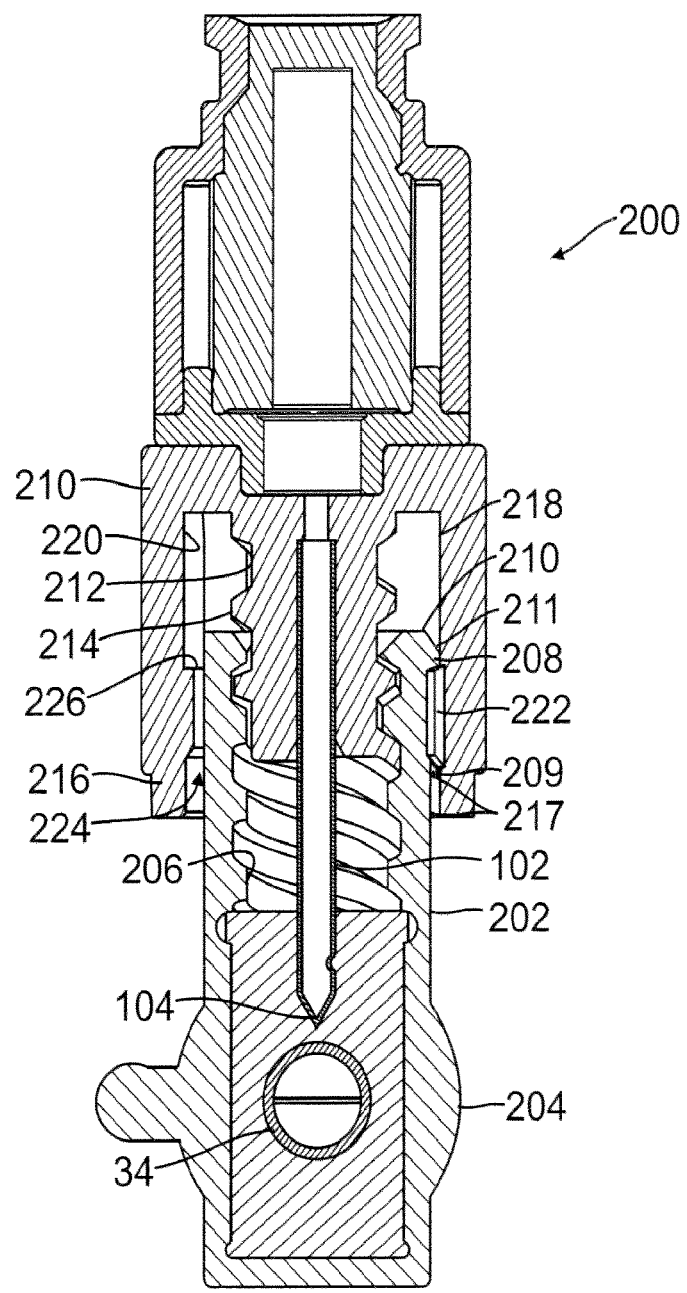
FIG. 4 is a right-side cross-sectional view of another embodiment of the present apparatus for selectively establishing a needleless injection port on IV tubing, illustrating the apparatus engaging IV tubing.
Figure 5:
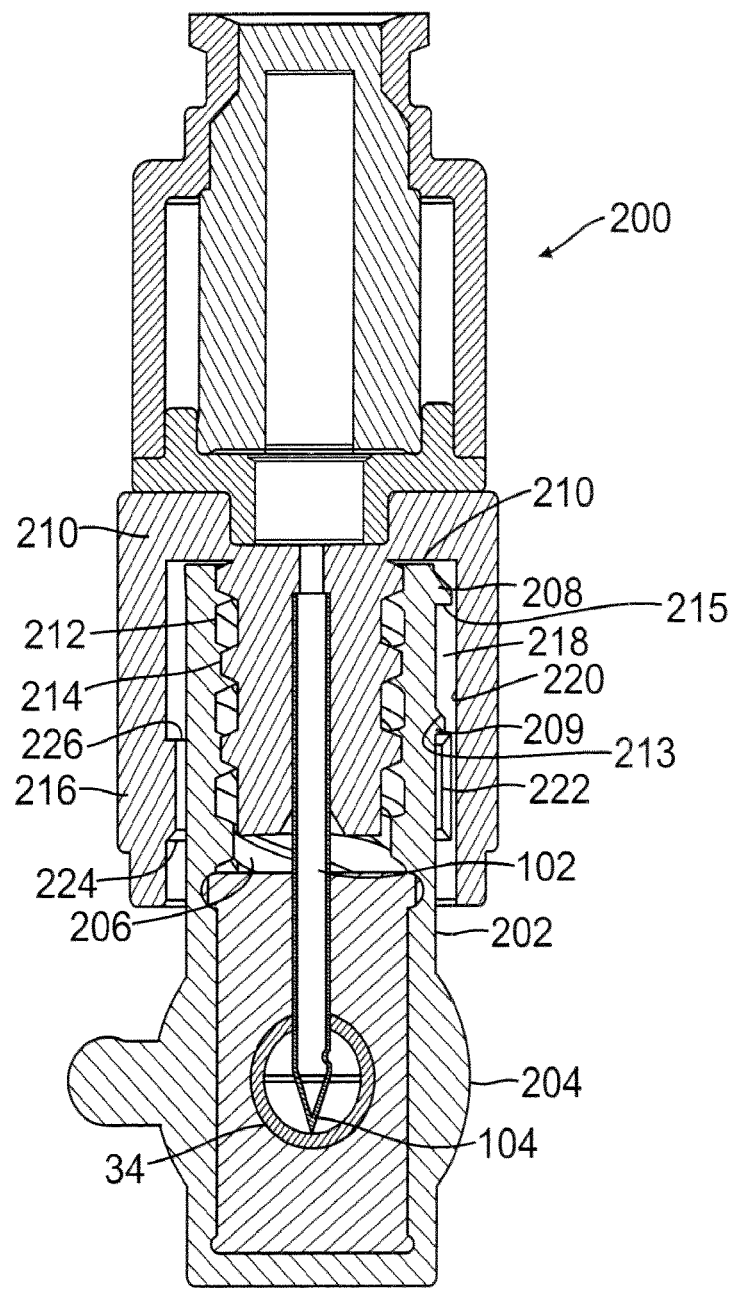
FIG. 5 is a right-side cross-sectional view of the apparatus of FIG. 4, illustrating a puncturing member of the apparatus penetrating the IV tubing.

FIGS. 4 and 5 illustrate another alternative embodiment of the present apparatus 200 for selectively establishing a needleless injection port on IV tubing. The embodiment of FIGS. 4 and 5 is similar to the embodiments of FIGS. 1-3. Accordingly, the description of the apparatus 200 herein will focus on the differences in structure between the embodiments. The apparatus 200 of FIGS. 4 and 5 includes a branch portion 202 extending perpendicularly from an IV tubing-engaging portion 204. The branch portion 202 includes internal threads 206, a first external flange 208 at a proximal end 207 and a second external flange 209 spaced distally from the first external flange 208. Each of the flanges includes a ramped proximal edge 211, 213 and a distal edge 215, 217 that extends perpendicularly to the branch portion 202.

The apparatus 200 further includes a piston portion 210 engaging the branch portion 202. The piston portion 210 includes a central shaft 212 having external threads 214 that mate with the internal threads 206 in the branch portion 202. Rotating the piston portion 210 in a first direction relative to the branch portion 202 causes the piston portion 210 to advance distally with respect to the branch portion 202, driving the puncturing member 102 through the sealing member and the IV tubing, as shown in FIG. 5.

The piston portion 210 further includes a cylindrical outer wall 216 separated from the central shaft 212 by an annular space 218. An interior surface 220 of the outer wall 216 includes an annular flange 222 having a ramped distal edge 224 and a proximal edge 226 that extends perpendicularly to the interior surface 220. When the apparatus 200 is in the configuration of FIG. 4, the distal edge 215 (FIG. 5) of the first flange 208 presents a barrier to the annular flange 222 on the outer wall 216, resisting proximal movement of the piston portion 210 relative to the branch portion 202. The flanges 208, 222 thus resist removal of the piston portion 210 from the branch portion 202.

When the piston portion 210 is rotated in the first direction relative to the branch portion 202, the ramped edges 213, 224 (FIG. 5) of the second flange 209 and the annular flange 222 ride up over one another as the piston portion 210 advances distally with respect to the branch portion 202. When the annular flange 222 passes the second flange 209, it snaps into place beneath the second flange 209, as shown in FIG. 5. The distal edge 217 (FIG. 4) of the second flange 209 presents a barrier to the annular flange 222 on the outer wall 216, resisting proximal movement of the piston portion 210 relative to the branch portion 202. The apparatus 200 is thus locked in a ready-to-use configuration in which the puncturing member 102 penetrates the IV tubing 34.

Figure 6:
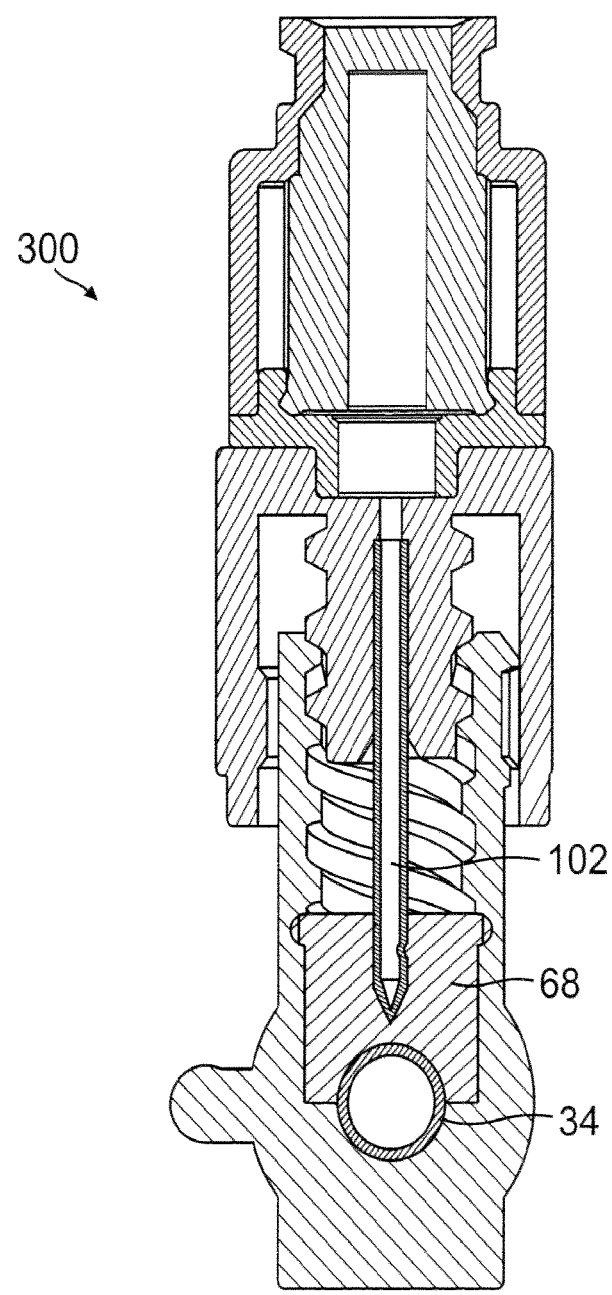
FIG. 6 is a right-side cross-sectional view of another embodiment of the present apparatus for selectively establishing a needleless injection port on IV tubing, illustrating the apparatus engaging IV tubing.
Figure 7:
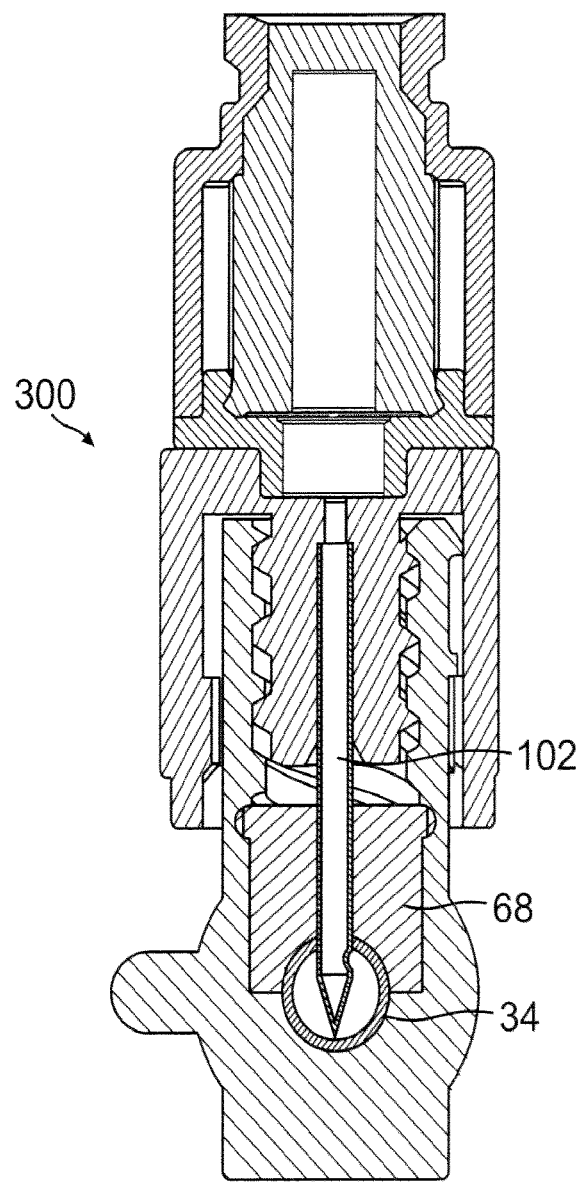
FIG. 7 is a right-side cross-sectional view of the apparatus of FIG. 6, illustrating a puncturing member of the apparatus penetrating the IV tubing.

FIGS. 6 and 7 illustrate another alternative embodiment of the present apparatus 300 for selectively establishing a needleless injection port on IV tubing. The embodiment of FIGS. 6 and 7 is similar to the embodiment of FIGS. 4 and 5. In the embodiment of FIGS. 6 and 7, however, the sealing member 68 is located on only the proximal side of the IV tubing 34. The sealing member 68 is located on the same side of the IV tubing 34 as the puncturing member 102. There is no corresponding sealing member 68 on the distal side of the IV tubing 34 opposite the puncturing member 102. The sealing member 68 nonetheless provides a leak-proof seal around the IV tubing 34 and the puncturing member 102 in the area where the puncturing member 102 punctures the IV tubing 34.

Figure 8:
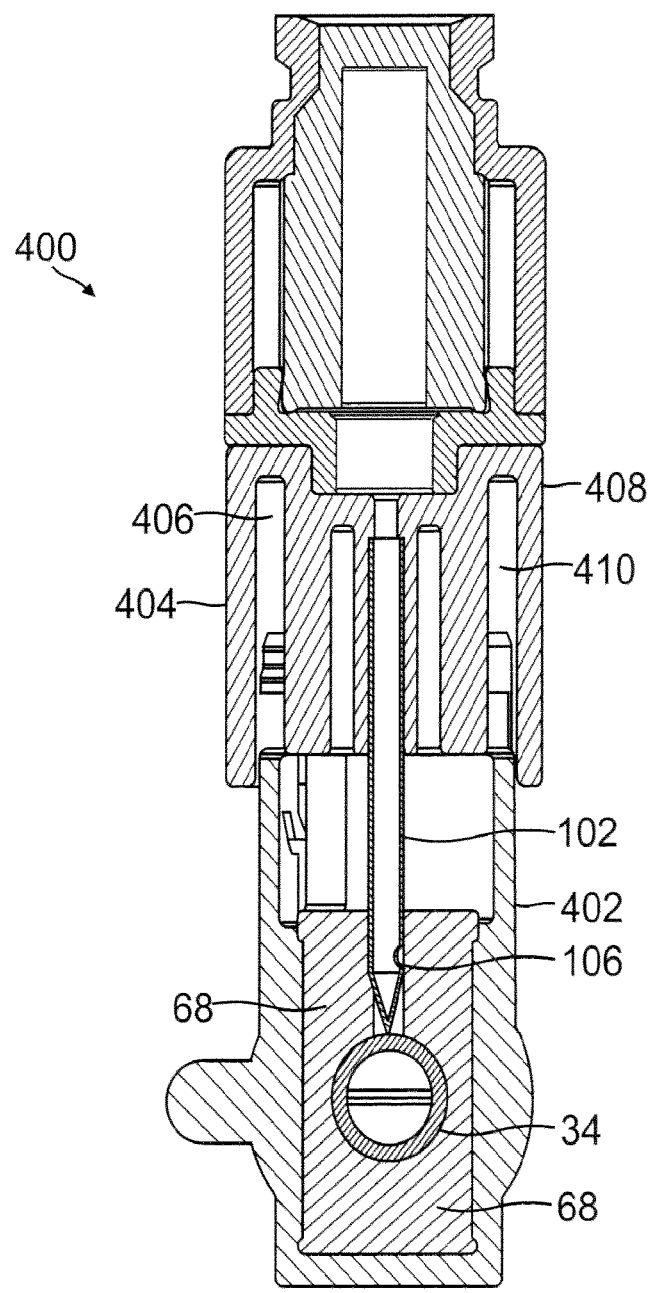
FIG. 8 is a right-side cross-sectional view of another embodiment of the present apparatus for selectively establishing a needleless injection port on IV tubing, illustrating the apparatus engaging IV tubing.
Figure 9:
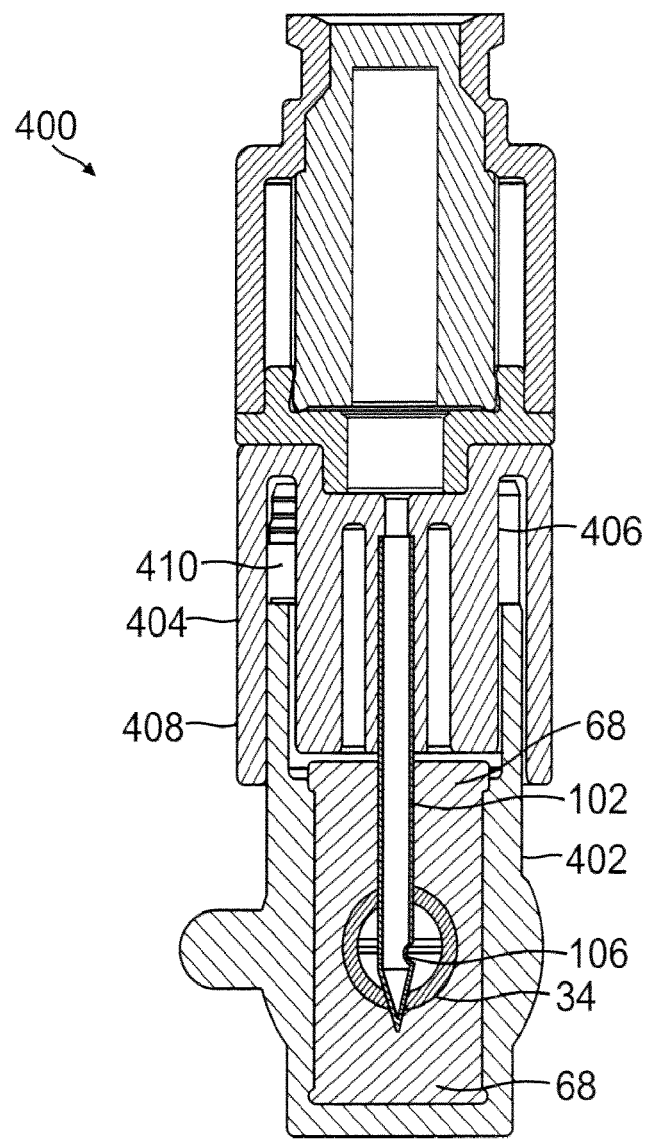
FIG. 9 is a right-side cross-sectional view of the apparatus of FIG. 8, illustrating a puncturing member of the apparatus penetrating the IV tubing.

FIGS. 8 and 9 illustrate another alternative embodiment of the present apparatus 400 for selectively establishing a needleless injection port on IV tubing. The embodiment of FIGS. 8 and 9 is similar to the embodiment of FIGS. 4 and 5. In the embodiment of FIGS. 8 and 9, however, neither the branch portion 402 nor the piston portion 404 includes threads. Instead, the branch portion 402 is shaped substantially as a smooth cylinder. The piston portion 404 includes a central shaft 406 that is also shaped substantially as a smooth cylinder and sized to fit within the branch portion 402. The piston portion 404 further includes a cylindrical outer wall 408 separated from the central shaft 406 by an annular space 410. The annular space 410 is sized to receive the branch portion 402 when the piston portion 404 is advanced distally with respect to the branch portion 402, as shown in FIG. 9.

In the embodiment of FIGS. 8 and 9, since neither the branch portion 402 nor the piston portion 404 includes threads, the piston portion 404 may be advanced distally with respect to the branch portion 402 by simply applying a pushing force to the piston portion 404. When the piston portion 404 advances far enough that the puncturing member 102 pierces the IV tubing 34 and the opening 106 in the puncturing member 102 is disposed within the IV tubing 34, a latching mechanism (not shown) on the branch portion 402 and the piston portion 404 may engage to restrict movement of the piston portion 404 proximally with respect to the branch portion 402, such as latching detents and interference knuckles or tabs.

With reference to FIG. 9, the puncturing member 102 passes completely through the IV tubing 34. However, the opening 106 is disposed within the IV tubing 34. Advancement of the puncturing member 102 may be controlled by providing physical stops or corresponding mating abutting surfaces between the various components, such as between the central shaft 406 and the sealing member 68. Thus, any liquid injected through the puncturing member 102 will pass into the IV tubing 34, rather than through it. Further, the apparatus 400 includes sealing members 68 that surround the IV tubing 34 in the area of the puncturing member 102. The sealing member 68 thus seals around both punctures in the IV tubing 34 to resist leakage of fluid from the IV tubing 34.

Figure 10:
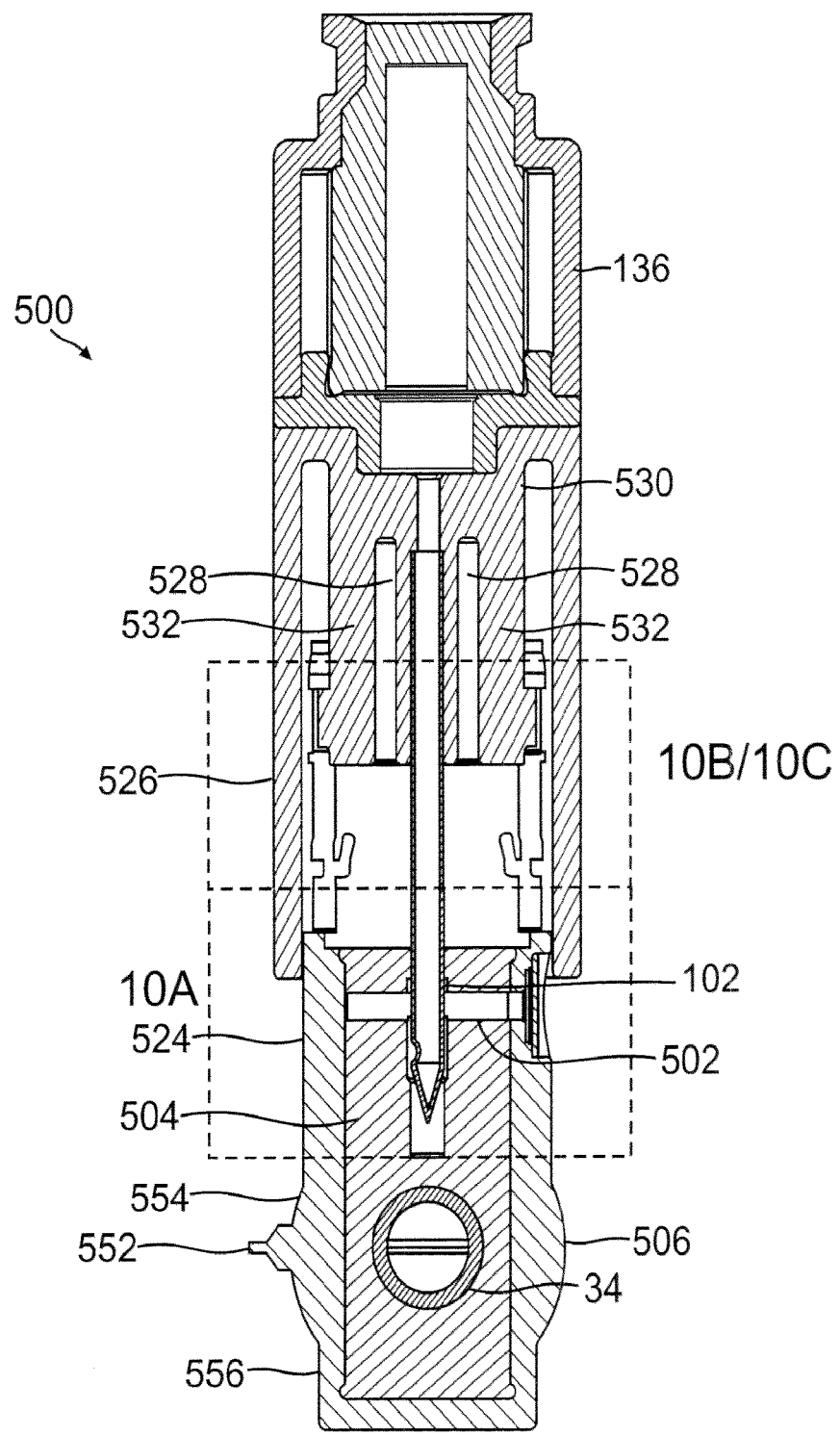
FIG. 10 is a right-side cross-sectional view of another embodiment of the present apparatus for selectively establishing a needleless injection port on IV tubing, illustrating the apparatus engaging IV tubing.
Figure 10A:
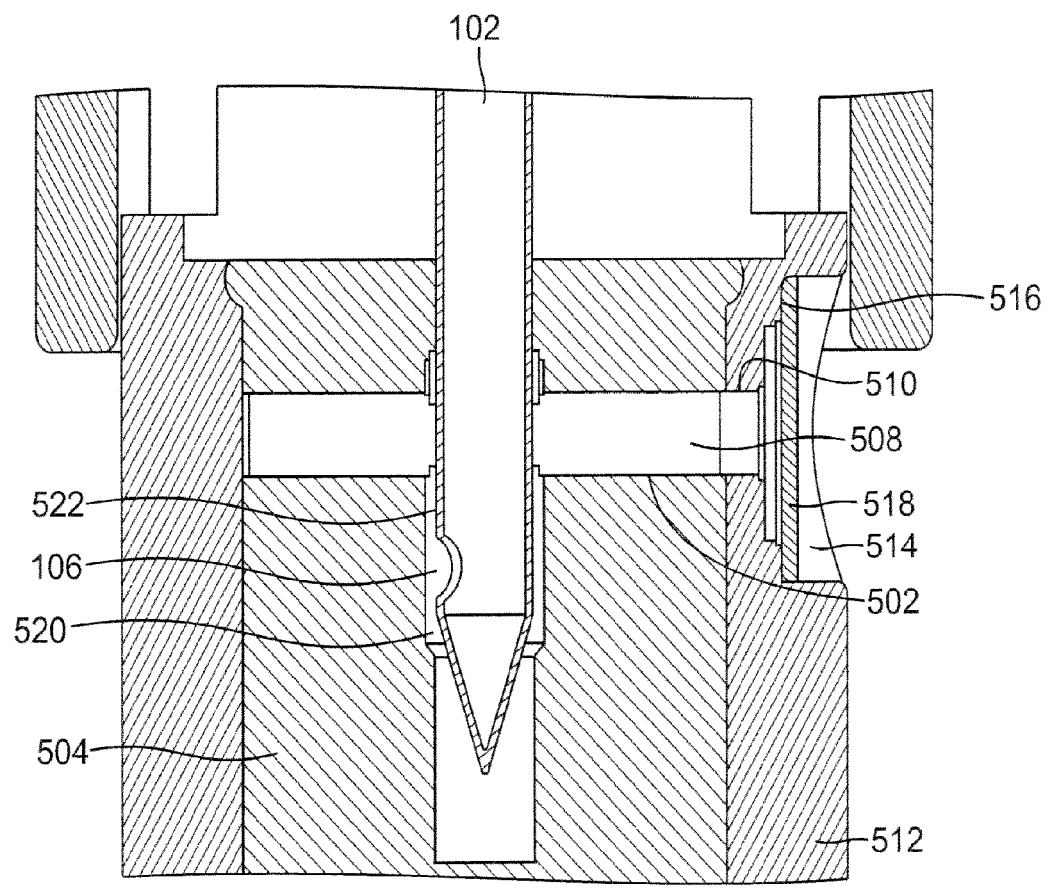
FIG. 10A is a detail view of the portion of FIG. 10 indicated by the box labeled 10A.
Figure 10B:
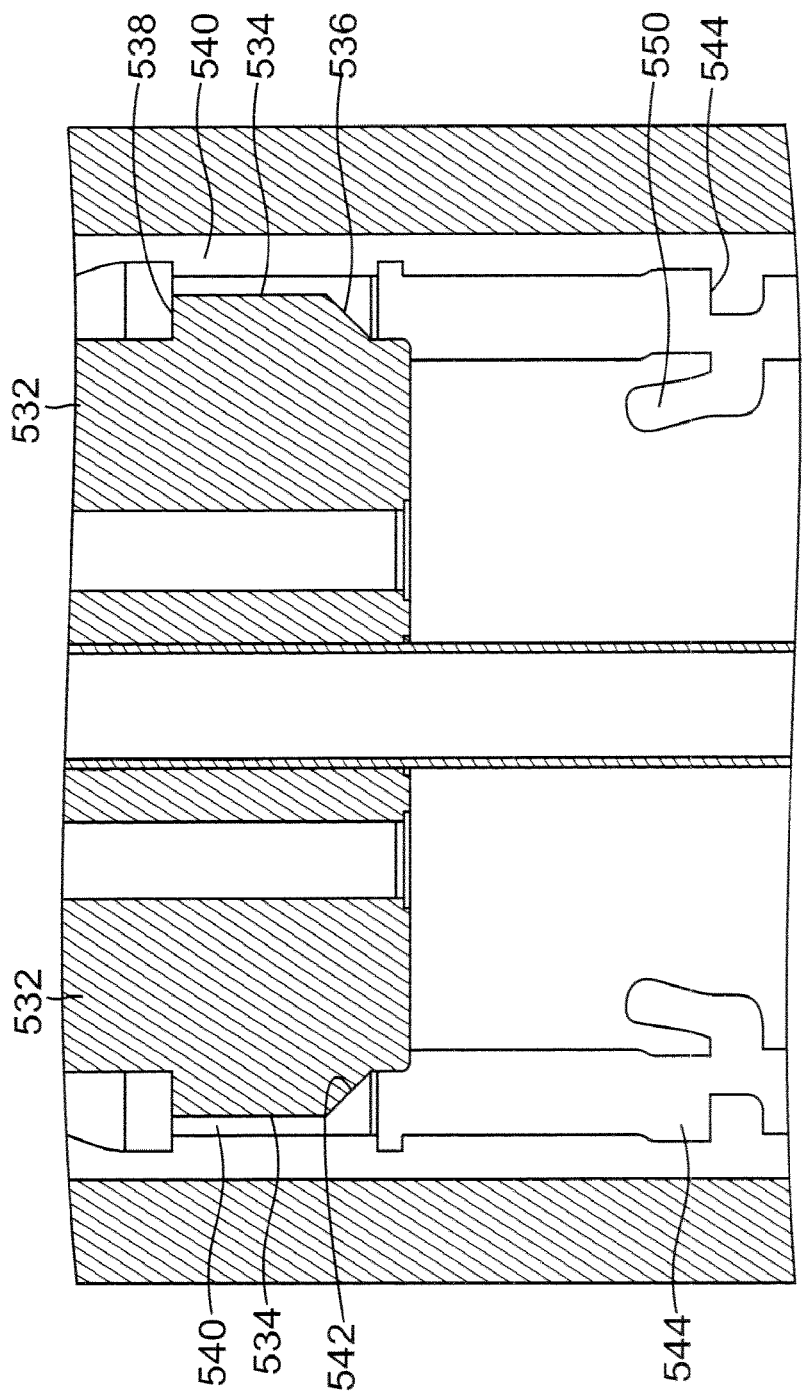
FIG. 10B is a detail view of one embodiment of the portion of FIG. 10 indicated by the box labeled 10B/10C.

FIGS. 10, 10A, 10B. 10C, 11 and 12 illustrate another alternative embodiment of the present apparatus 500 for selectively establishing a needleless injection port on IV tubing 34. The embodiment of FIGS. 10, 10A, 10B, 10C, 11 and 12 is similar to the embodiment of FIGS. 8 and 9. The embodiment of FIGS. 10, 10A, 10B, 10C, 11 and 12, however, includes a priming channel 502. With reference to FIG. 10A, the priming channel 502 extends through the sealing member 504 in a direction transverse to the puncturing member 102 and transverse to a longitudinal axis of the IV tubing-engaging portion 506 but may alternatively be parallel. The priming channel 502 is located on the proximal side of the IV tubing 34 when the apparatus 500 is secured to the IV tubing 34.

With continued reference to FIG. 10A, a first end of the priming channel 502 comprises an aperture 510 in the first section 512 of the IV tubing-engaging portion 506. The aperture 510 adjoins a recess 514 in the outer surface of the first section 512. The recess 514 includes an annular shoulder 516 that retains a hydrophobic porous membrane 518. The porous membrane 518 includes openings (not shown) that are configured to enable gaseous particles (such as the constituents of air) to pass, but not liquid particles (such as water). The membrane 518 thus provides a partial seal over the priming channel 502 by enabling air, but not liquid, to escape the interior of the apparatus 500. Hydrophobic filters can be made from a number of suitable materials well known to one skilled in the art, such as from super hydrophobic polyvinyldiflouride (PVDF).

With continued reference to FIG. 10A, the sealing member 504 on the proximal side of the IV tubing 34 includes a recess 520 that is sized and shaped to receive the distal region 522 of the puncturing member 102. The recess 520 is slightly larger in diameter than the puncturing member 102 so that the sealing member 504 does not form a seal over the opening 106 in the puncturing member 102 when the distal region 522 of the puncturing member 102 is disposed in the recess 520.

When the distal region 522 of the puncturing member 102 is disposed in the recess 520 as shown in FIG. 10A, the apparatus 500 may be primed as follows. The operator connects a syringe (not shown) to the valve member 136 (FIGS. 10 and 11) in the manner described above with respect to the embodiments of FIGS. 1-3. The operator then injects liquid from the syringe into the apparatus 500. The injected liquid enters the lumens 100, 150, 152 (See e.g., FIG. 3A) and the lumen in the puncturing member 102 and displaces any air contained there. With reference to FIG. 10A, the air flows from the lumens out the opening 106 in the distal region of the puncturing member 102, into the priming channel 502, and finally out through the porous membrane 518. The membrane 518 allows gaseous particles to pass, but not liquid. Thus, the inflowing liquid forces all (or substantially all) entrained air in the lumens and the priming channel 502 and recess 520 out of the apparatus 500.

Once the air is forced out, the operator can advance the piston portion 526 with respect to the branch portion 524 in order to pierce the IV tubing 34, and then proceed to inject liquid medicine. The operator may, for example, inject medicine using the same syringe that he or she used to prime the apparatus 500. Alternatively, the operator may prime the apparatus 500 with a first syringe containing, for example, saline. The operator may then disconnect the first syringe from the valve member 136, connect a second syringe to the valve member 136, and make the injection using the second syringe. However, as air space or dead space inside the valve member is relative small, purging is not believed to be mandatory.

With embodiments of the present apparatus that do not include a priming channel 502, an operator can still prime the apparatus prior to injection as follows. With reference to FIG. 5, for example, the operator advances the piston portion 210 distally relative to the branch portion 202 until the opening 106 in the distal region of the puncturing member 102 is disposed within the IV tubing 34. The operator can perform this step before or after connecting a syringe to the valve member 136. With the syringe connected, the operator draws back on the syringe plunger to withdraw liquid from the interior of the IV tubing 34. The liquid flows through the lumens, forcing air out and into the syringe. When the operator observes that liquid begins to flow into the syringe from the apparatus 500, he or she knows that all (or substantially all) of the air has been expelled from the lumens. The operator then disconnects the syringe. However, purging may be eliminated altogether due to the relatively small head space.

If the syringe contains the medicine to be injected, the operator orients the syringe with its outlet port facing upward so that the air in the syringe migrates upward. He or she then expels the air from the syringe, reconnects the syringe to the valve member, and injects the medicine. Alternatively, if the syringe is empty or contains a liquid other than the medicine to be injected, the operator discards the syringe and connects a different syringe (containing the medicine) to the valve member. The operator then injects the medicine.

Figure 10C:
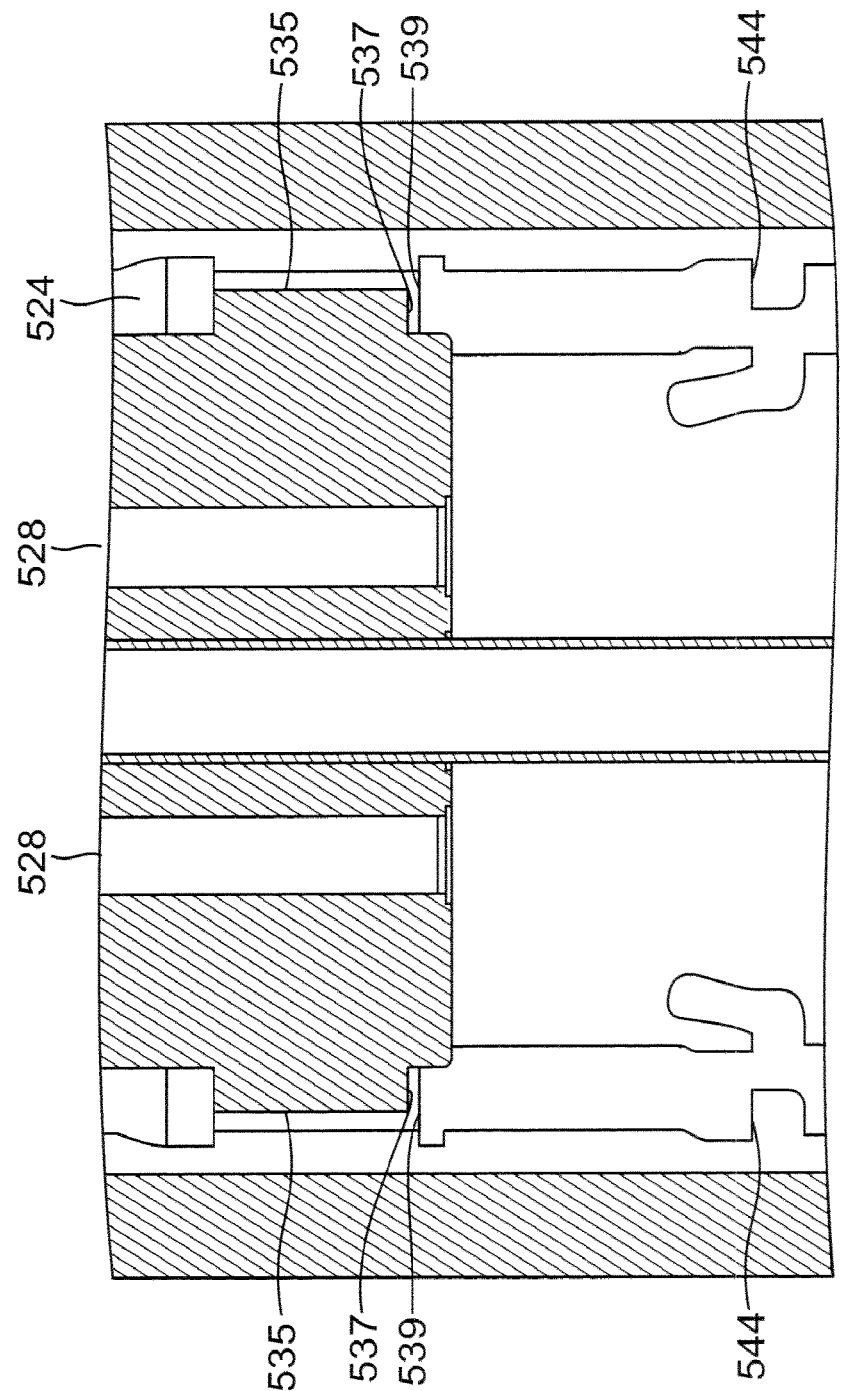
FIG. 10C is a detail view of another embodiment of the portion of FIG. 10 indicated by the box labeled 10B/10C.
Figure 11:
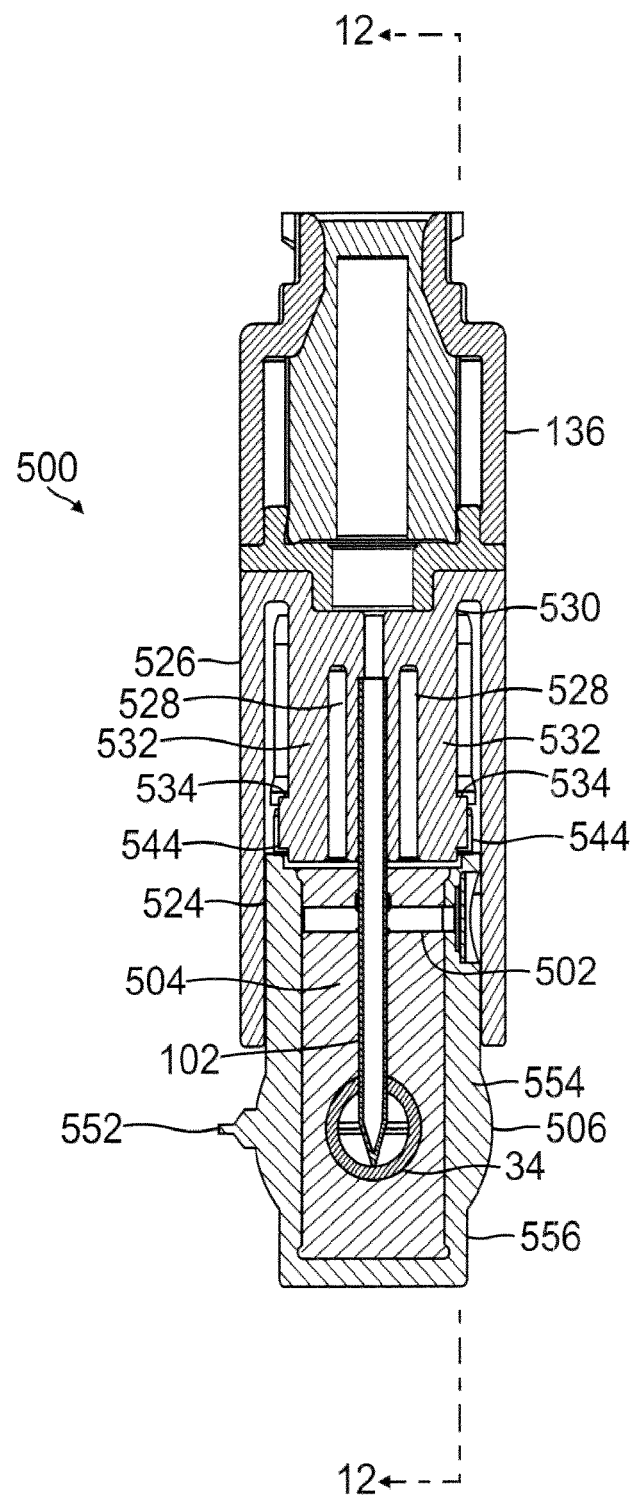
FIG. 11 is a right-side cross-sectional view of the apparatus of FIG. 10, illustrating a puncturing member of the apparatus penetrating the IV tubing.

With reference to FIGS. 10, 10B, 10C, 11 and 12, the apparatus 500 further includes a latching mechanism configured to retain the apparatus 500 in the configuration of FIG. 11. With particular reference initially to FIG. 10, first and second cavities 528 extend longitudinally and transversely through the central shaft 530 of the piston portion 526 on either side of the puncturing member 102. In one embodiment, shown particularly in FIG. 10B, the cavities 528 marked a divide of the central shaft 530 as first and second cantilevered, distally extending legs 532. Each of the legs 532 includes surface features, described below, on its outer surface. Said differently, in the present embodiment, the central shaft 530 is shaped as two cantilevered extending legs having gaps therebetween. In other embodiments, as further discussed below, the central shaft is shaped as a generally elongated cylinder.

Figure 12:
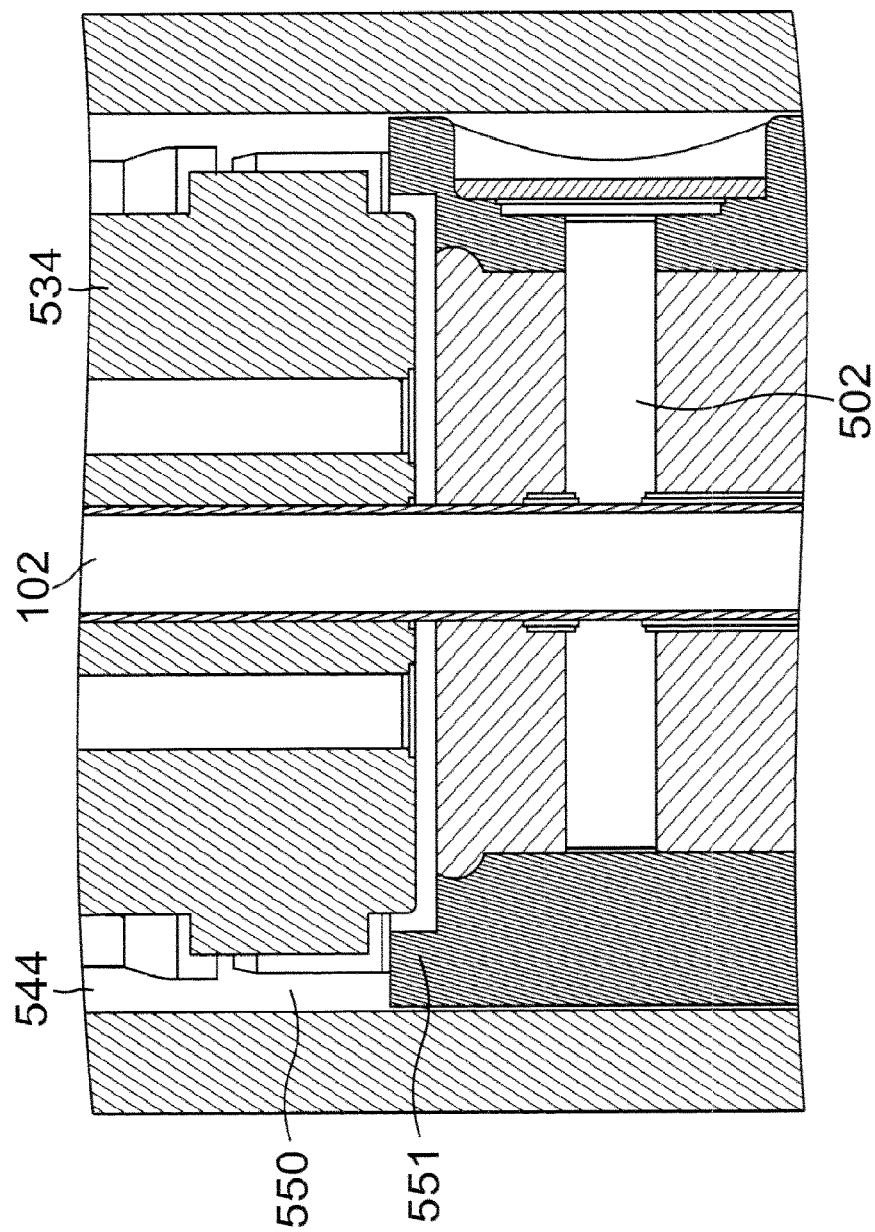
FIG. 12 is a front cross-sectional view of the apparatus of FIG. 11 taken through the line 12-12 in FIG. 11.

With reference to FIG. 10B, the surface features include a tab 534 having a ramped distal surface 536 and a proximal surface 538 extending perpendicularly to the leg 532. First recesses 540 in the branch portion 524 receive the tabs 534. The first recesses 540 include ramped distal surfaces 542 so that when the operator applies force to the piston portion 526 to advance it distally with respect to the branch portion 524 the engagement of the ramped surfaces 536, 542 urges the legs 532 to bow inwardly, disengaging the tabs 534 from the first recesses 540. When the piston portion 526 approaches the position shown in FIG. 11, the tabs 534 engage cantilevered arms 544, shown in FIG. 12. The cantilevered arms 544 are formed by cutouts 550 in the sidewall of the branch portion 524 that are positioned behind the cantilevered arms 544. The cantilevered arms 544 extend into the path of the tab 534 as it moves distally, as shown in FIG. 12. Thus, when the tab 534 engages the cantilevered arms 544 it bends them outwardly into the cutouts 550, thereby clearing a path for the tab 534. When the tab 534 reaches the space 551 beneath the cantilevered arms 544, the arms 544 snap back to their original shape and block the return path of the tab 534. Engagement of the cantilevered arms 544 with the tabs 534 thus resists proximal movement of the piston portion 526 with respect to the branch portion 524. The tabs 534 and cantilevered arms 544 thus hold the apparatus 500 in the configuration of FIG. 11, in which the opening 106 in the distal region of the puncturing member 102 is disposed within the IV tubing 34.

Figure 12A:
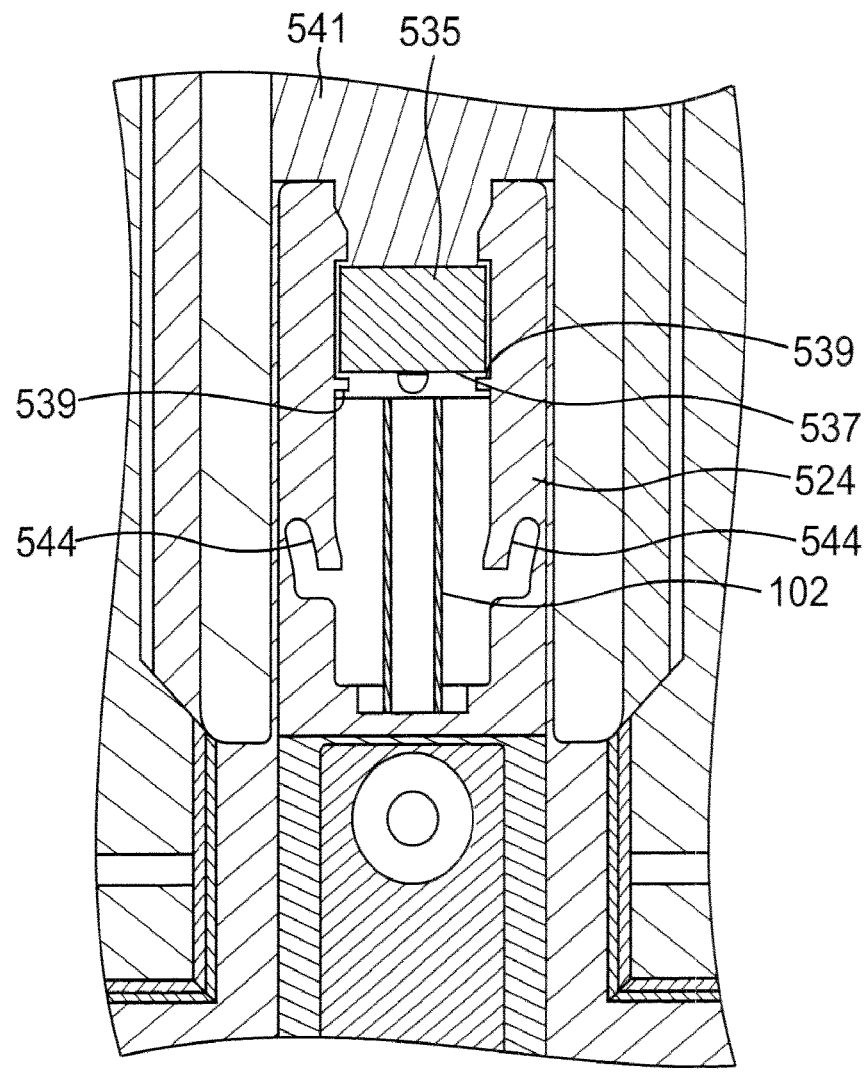
FIG. 12A is an alternative front cross-sectional view of the apparatus of FIG. 11 taken through the line 12-12 in FIG. 11.

FIGS. 10C and 12A illustrate an alternative embodiment in which the tabs 535 include distal surfaces 537 that are not ramped. The distal surfaces 537 engage frangible tabs 539 on the branch portion 524. When the operator applies a distally directed force to the piston portion 541, the tabs 535 bear against the frangible tabs 539, which snap off when a threshold force is reached. The piston portion 541 then advances distally until the tabs 535 become entrained beneath the cantilevered arms 544 as described above with respect to FIGS. 10B and 12. In the embodiment of FIGS. 10C and 12A, the first and second cavities 528 may or may not divide the piston portion 541 into first and second legs, as in the previous embodiment.

With reference to FIGS. 10 and 11, the apparatus 500 further includes an alternative hinge 552 connecting the first and second sections 554, 556 of the IV tubing-engaging portion 506. In contrast to the hinge 48 of the previous embodiments, which includes first and second cylindrical hinge parts 50, 52, the hinge 552 of FIGS. 10 and 11 is a living hinge. A living hinge is a thin flexible member that joins two rigid parts together, allowing them to bend along the line of the hinge. Those of ordinary skill in the art will appreciate that the living hinge 552 of the illustrated embodiment is not limited to any particular material or method of manufacture.

Figure 13:
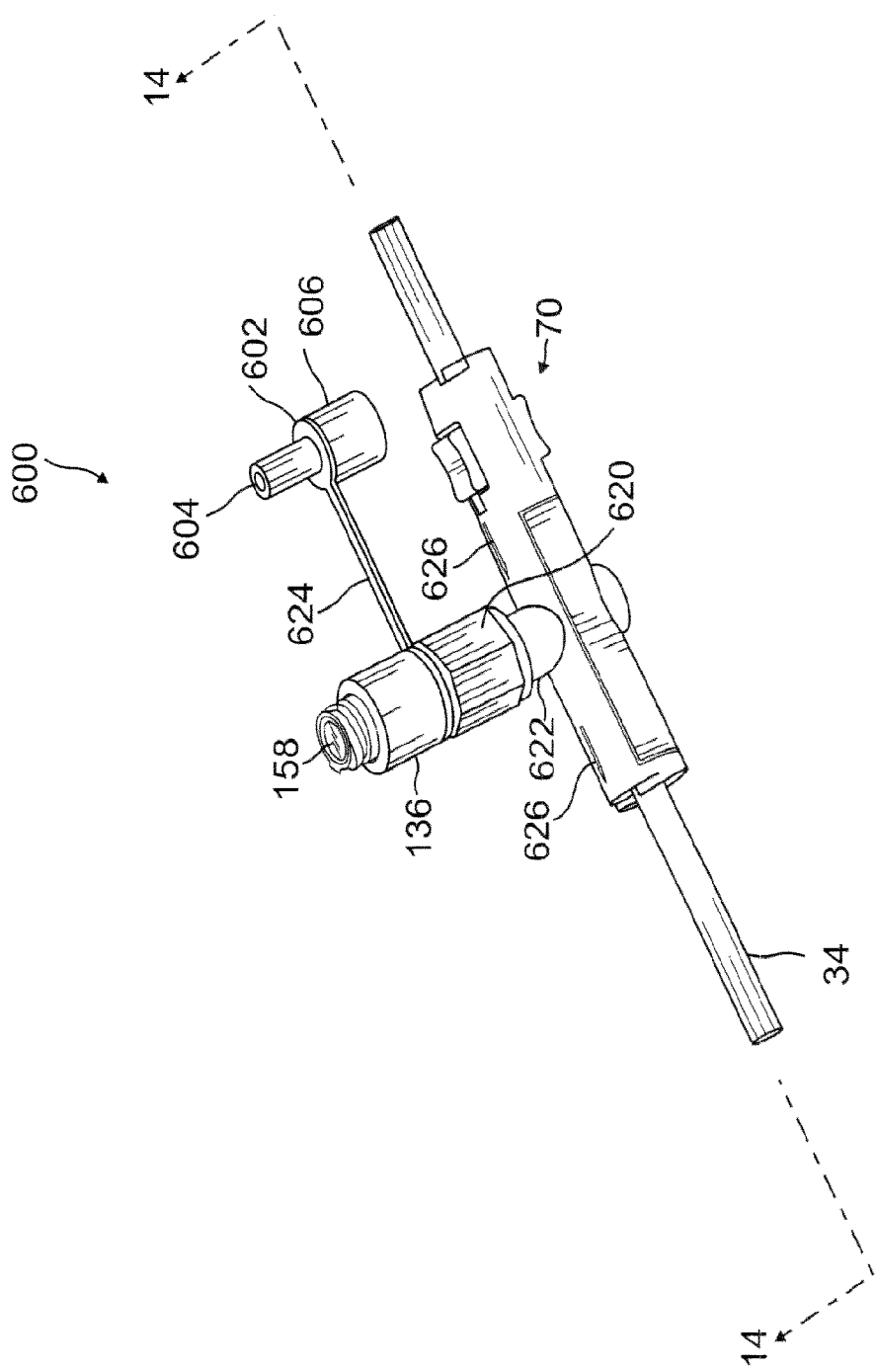
FIG. 13 is a rear perspective view of another embodiment of the present apparatus for selectively establishing a needleless injection port on IV tubing, illustrating the apparatus engaging IV tubing.
Figure 14:
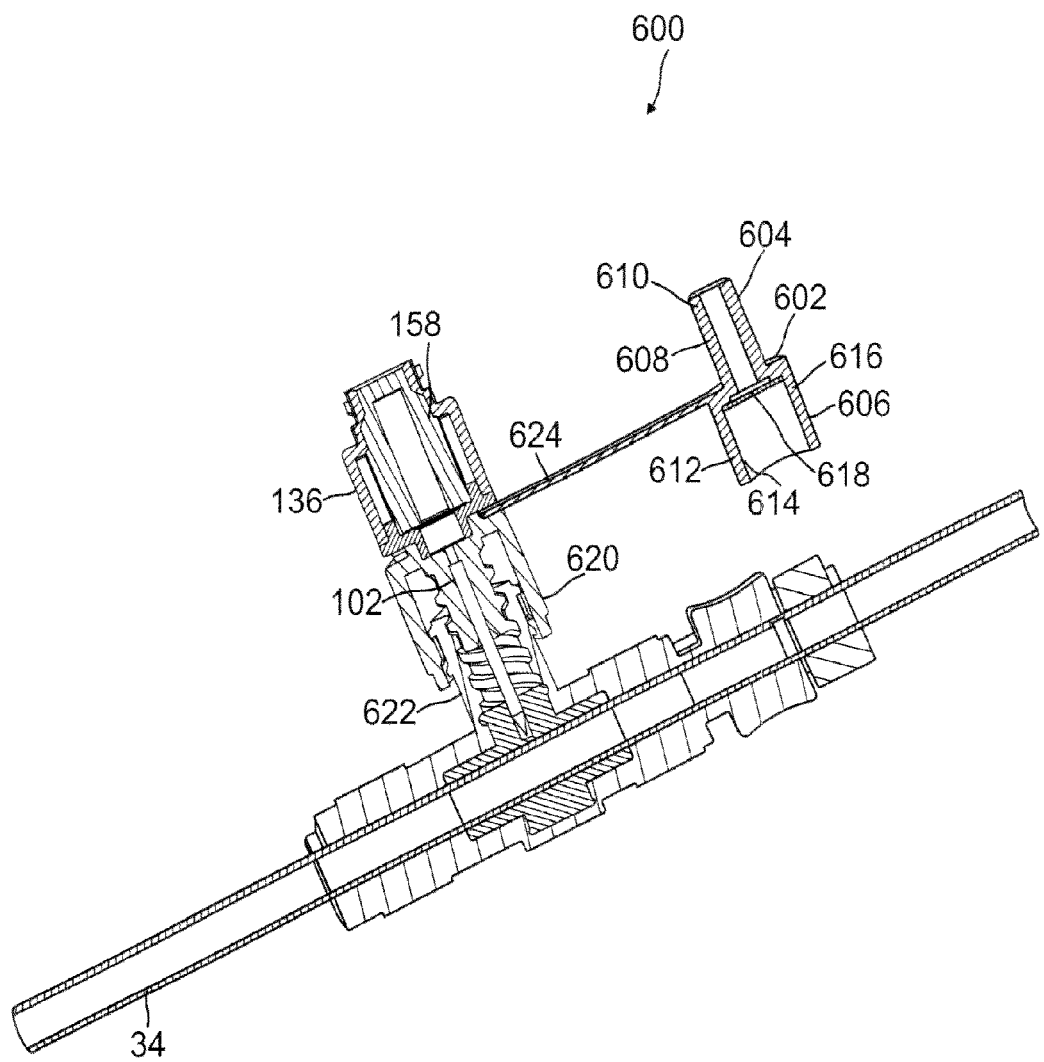
FIG. 14 is a rear cross-sectional view of the apparatus of FIG. 13 taken through the line 14-14 in FIG. 13.

FIGS. 13 and 14 illustrate another alternative embodiment of the present apparatus 600 for selectively establishing a needleless injection port on IV tubing. The embodiment of FIGS. 13 and 14 is similar to the embodiments described above, but includes a priming valve 602. The priming valve 602 comprises a stepped cylinder including a distal region 604 and a proximal region 606. With reference to FIG. 14, the distal region 604 comprises a male nozzle 608 having a tapered outer surface 610 that is configured to penetrate the valve member 136. The proximal region 606 comprises a female connector 612 having a tapered inner surface 614 that is configured to receive a male nozzle on a syringe (not shown). An annular shoulder 616, comprising an abrupt change in diameter, demarcates the junction of the distal and proximal regions 604, 606. The annular shoulder 616 supports a porous membrane 618, which is similar in structure and function to that described above. In a specific embodiment, the tapered surfaces are formed as Luer tapered surfaces.

To prime the apparatus 600 using the priming valve 602, an operator inserts the male nozzle 608 into the valve member 136 to open fluid communication through the sealing member 158. The operator then engages a syringe (not shown) with the female connector 612 to achieve a seal between a tapered outer surface of a male nozzle of the syringe and the tapered inner sidewall 614 of the female connector 612. The operator then advances the piston portion 620 with respect to the branch portion 622 to pierce the IV tubing 34 with the puncturing member 102. Those of ordinary skill in the art will appreciate that the previously described steps may be performed in any order. Also, the piercing member may be advanced to puncture the IV tubing without having to first insert the valve opener and/or the syringe or other medical implement.

With the puncturing member 102 piercing the IV tubing 34, the male nozzle 608 opening fluid communication through the sealing member 158, and the syringe connected to the priming valve 602, the operator then pulls back on a plunger of the syringe to draw air out of the lumens. Liquid flowing out of the IV tubing 34 forces the air out of the lumens, through the porous membrane 618 and into the syringe. Since the membrane 618 will not allow liquid particles to pass, the operator knows that all (or substantially all) of the air has been expelled from the lumens when the force required to draw back the plunger increases sharply. The operator then withdraws the syringe from the priming valve 602 and withdraws the priming valve 602 from the valve member 136. He or she then injects medicine using the syringe (or a second syringe) as described above with respect to the previous embodiments.

In the illustrated embodiment, a tether 624 secures the priming valve 602 to the apparatus 600. As shown, the tether 624 is molded as a single piece with the priming valve 602, and is secured to the piston portion 620 at an end spaced from the priming valve 602. Those of ordinary skill in the art will appreciate that the illustrated configuration for the tether 624 is only one example. Those of ordinary skill in the art will further appreciate that in embodiments including a priming valve 602 a tether 624 is optional.

The apparatus 600 of FIGS. 13 and 14 further includes indicia 626 (FIG. 13) that assist the operator in properly positioning the apparatus 600 on the IV tubing 34. In the illustrated embodiment, the indicia 626 comprises at least one arrow. The arrow indicates the desired direction of flow through the apparatus 600, so that the clamp 70 is positioned at the upstream end of the apparatus 600. Those of ordinary skill in the art will appreciate that any of the embodiments described herein may also include indicia.

Figure 15:
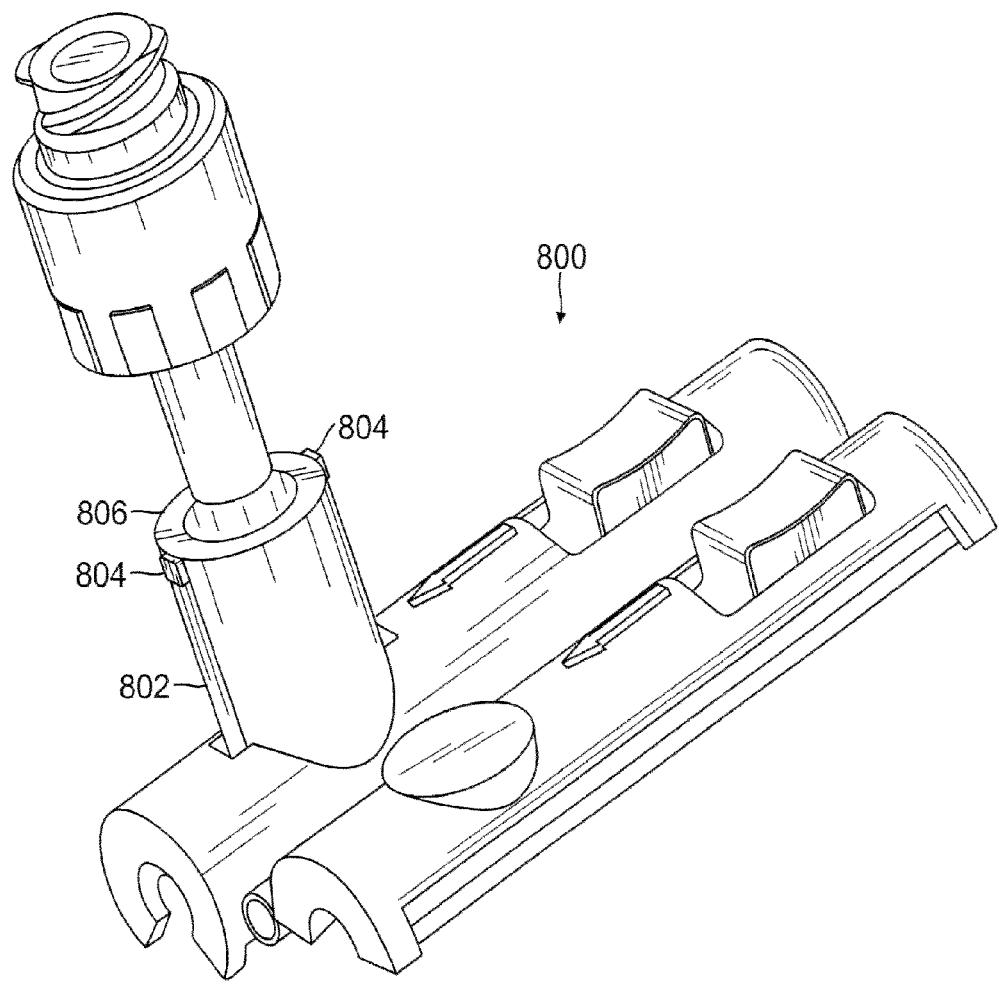
FIG. 15 is a front perspective view of another embodiment of the present apparatus for selectively establishing a needleless injection port on an IV tubing.
Figure 16:
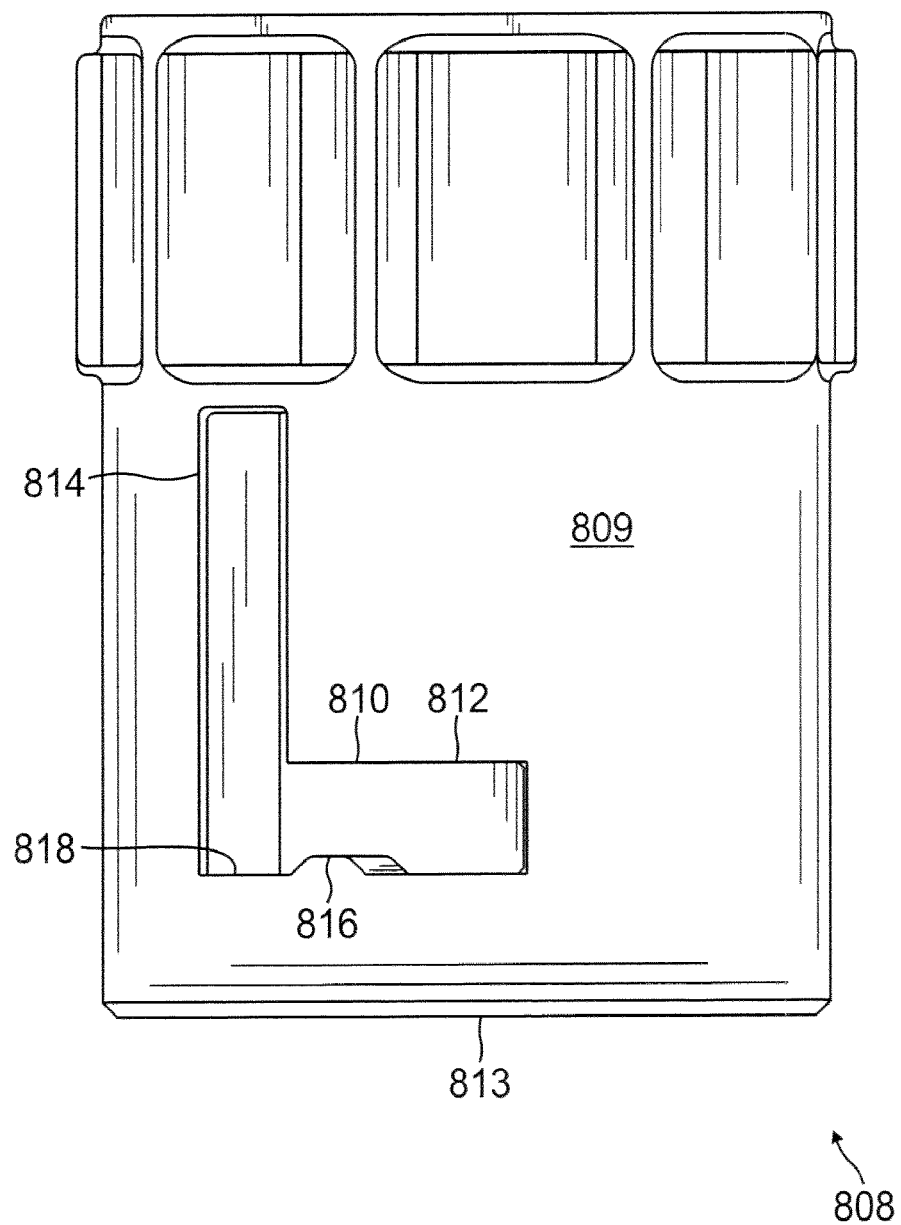
FIG. 16 is a front elevation view of a piston portion configured for use with the apparatus of FIG. 15.
Figure 17:
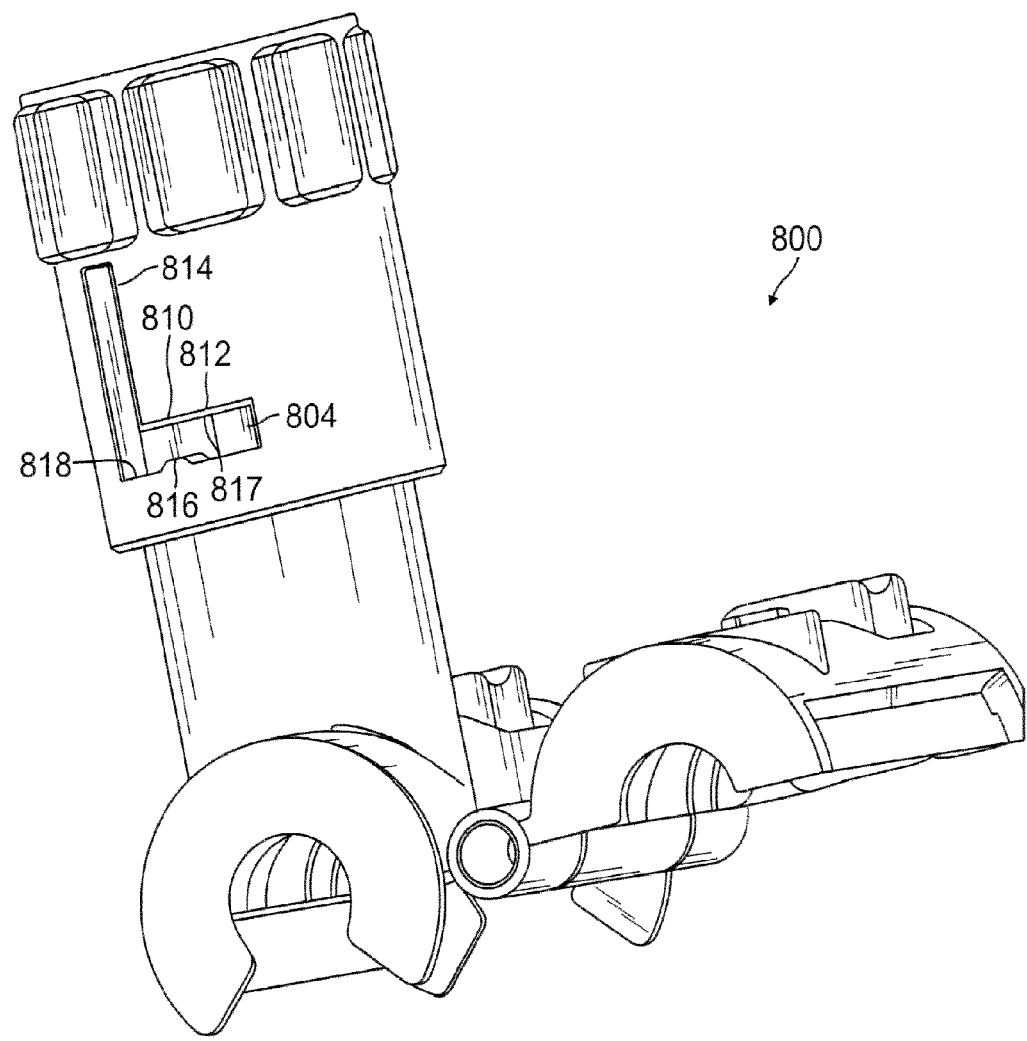
FIG. 17 is a front perspective view of the apparatus of FIG. 15 in combination with the piston portion of FIG. 16.

FIGS. 15-17 illustrate another alternative embodiment of the present apparatus 800 for selectively establishing a needleless injection port on IV tubing. The embodiment of FIGS. 15-17 is similar to the embodiment described above and illustrated in FIGS. 8 and 9. However, as shown in FIG. 15 the branch portion 802 of the apparatus 800 includes first and second tabs 804 at its proximal end 806. The tabs 804 extend outwardly from opposite sides of the proximal end 806 but may be placed at different locations in other embodiments.

With reference to FIG. 16, a sidewall 809 of the piston portion 808 of the apparatus 800 includes an L-shaped channel 810 that receives one of the tabs 804, as shown in FIG. 17. While not shown in the figures, the sidewall 809 includes a second L-shaped channel opposite the illustrated channel 810, or at a location that corresponds to the second tab on the branch portion 802. The second L-shaped channel receives the other tab 804. Those of ordinary skill in the art will appreciate, however, that in alternative embodiments the branch portion 802 may include only one tab 804 and the piston portion 808 may include only one L-shaped channel 810. In still further alternative embodiments, the branch portion 802 may include more than two tabs 804 and the piston portion 808 may include a corresponding number of L-shaped channels 810.

With reference to FIG. 16, the L-shaped channel 810 includes a first branch 812 that extends circumferentially about the sidewall 809 and a second branch 814 that extends longitudinally along the sidewall 809. The first branch 812 is located adjacent a distal end 813 of the piston portion 808. The first and second branches 812, 814 connect at a ninety-degree angle at an end of each branch, with the second branch 814 extending proximally along the sidewall 809 from the first branch 812. The channel 810 extends completely through the sidewall 809, and has a substantially constant width. However, the first branch 812 includes a boss 816 that narrows the width of the first branch 812 in the region of the boss 816. The boss 816 is flat on top, and ramped on either side.

With reference to FIG. 17, when the piston portion 808 is located at its proximal extreme along the branch portion 802, the first branch 812 receives the tab 804. The tab 804 provides a barrier preventing the piston portion 808 from translating distally along the branch portion 802. A pushing force applied to the piston portion 808 in a distal direction causes the tab 804 to bear against the proximal wall 817 of the first branch 812. The tab 804 and the first branch 812 thus resist accidental distal translation of the piston portion 808 along the branch portion 802.

The tab 804 and boss 816 provide additional resistance to accidental distal translation of the piston portion 808 along the branch portion 802. When the apparatus 800 is shipped, the tab 804 is located on an opposite side of the boss 816 from the second branch 814. The tab 804, the first branch 812 and the boss 816 are all shaped and dimensioned so that the boss 816 provides a surmountable barrier to movement of the tab 804 through the first branch 812. Thus, when the operator rotates the piston portion 808 about the branch portion 802, the tab 804 rides up over the boss 816 and squeezes through the narrow width of the first branch 812 in the region of the boss 816. As the operator continues rotating the piston portion 808 in the same direction about the branch portion 802, the tab 804 eventually reaches the distal end 818 of the second branch 814. The tab 804 can then slide freely through the second branch 814 as the piston portion 808 translates distally along the branch portion 802.

Figure 18:
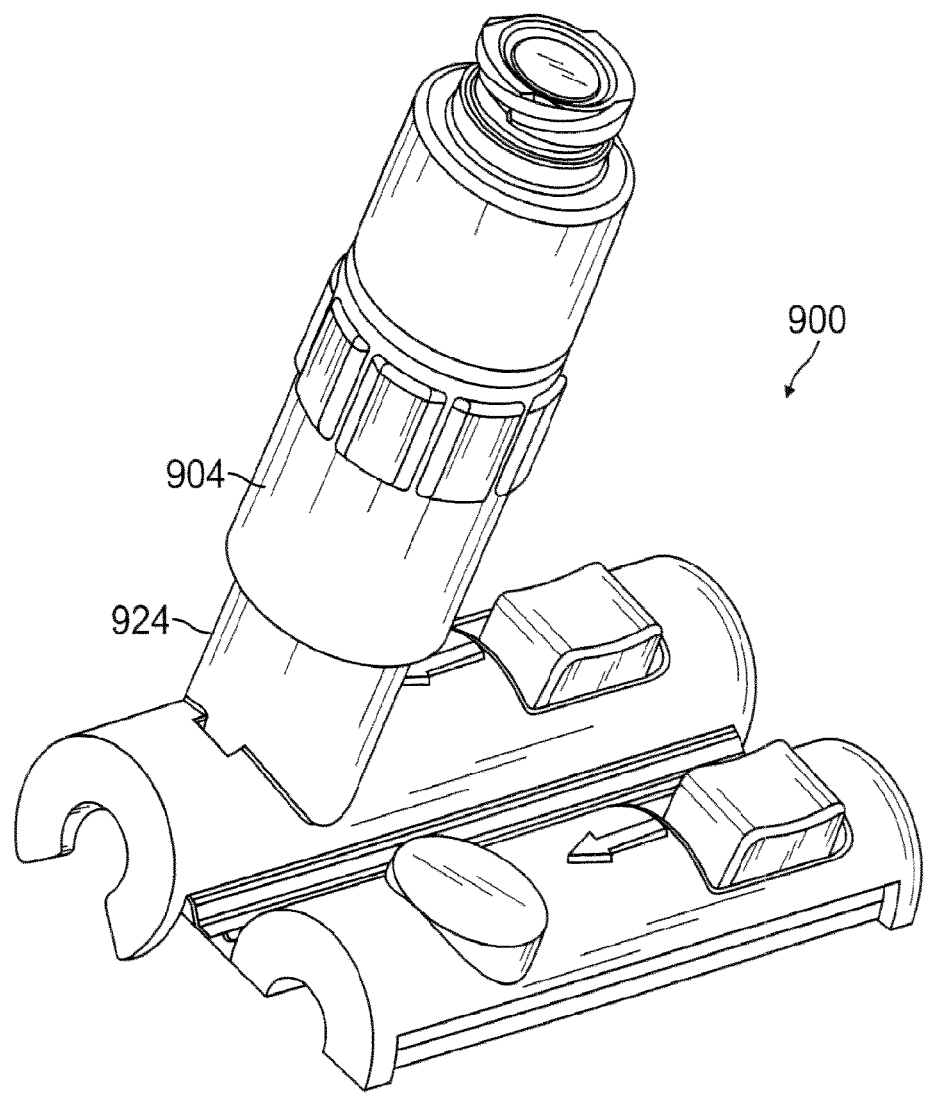
FIG. 18 is a front perspective view of another embodiment of the present apparatus for selectively establishing a needleless injection port on an IV tubing.
Figure 19:
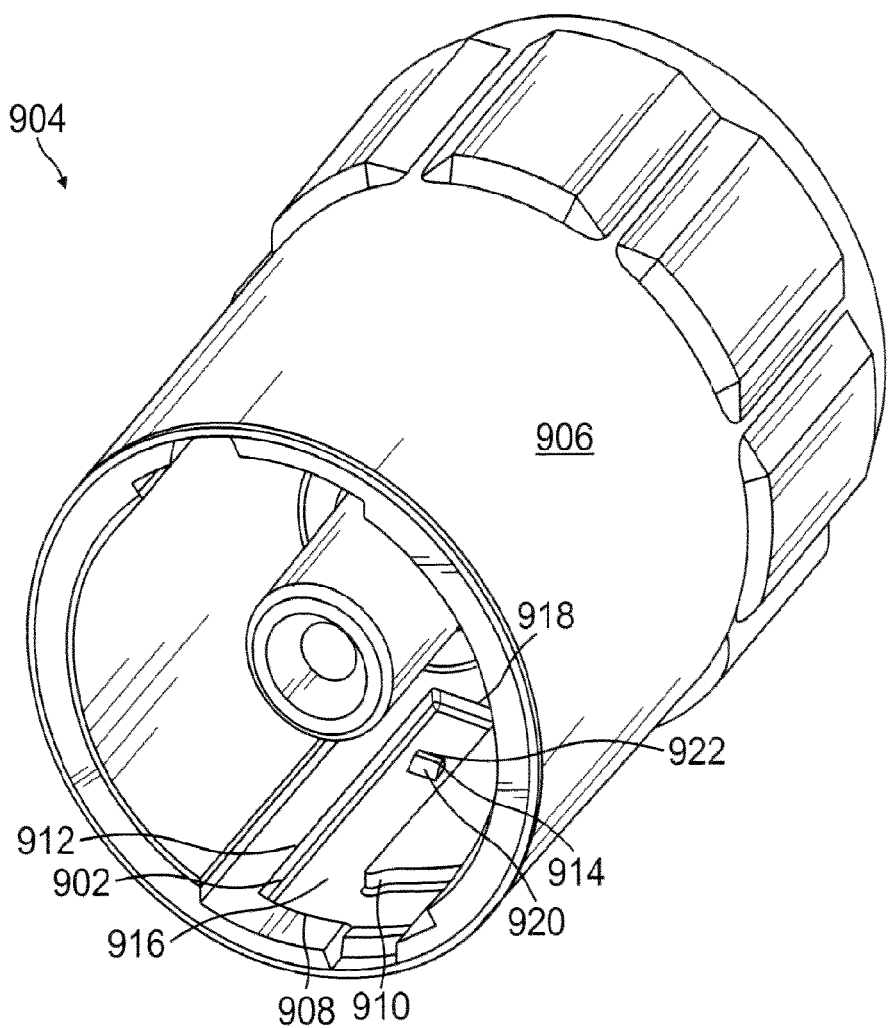
FIG. 19 is a lower perspective view of the piston portion of the apparatus of FIG. 18.

FIGS. 18 and 19 illustrate another alternative embodiment of the present apparatus 900 for selectively establishing a needleless injection port on IV tubing. The embodiment of FIGS. 18 and 19 is similar to the embodiment described above and illustrated in FIGS. 15-17. However, as shown in FIG. 19 the L-shaped channels 902 in the piston portion 904 do not pass completely through the sidewall 906. Only one of the channels 902 is visible in FIG. 19.

A first branch 908 of the channel 902 includes a boss 910 that functions in the same manner as the boss 816 described above with respect to FIGS. 15-17. However, in the piston portion 904 of FIG. 19 the boss 910 is located at the interior corner of the intersection of the first branch 908 and the second branch 912.

With continued reference to FIG. 19, the second branch 912 includes a detent 914 in its floor 916. The detent 914 is spaced from a proximal end 918 of the second branch 912, and includes a ramped distal surface 920. A proximal surface 922 of the detent 914 is oriented perpendicularly to the floor 916. The detent 914 thus enables the tab 804 to ride over the ramped distal surface 920 and snap into place proximally of the detent 914 where the proximal surface 922 resists movement of the tab 804 distally of the detent 914. The detent 914 thus locks the piston portion 904 in its extreme distal position relative to the branch portion 924.

Figure 20:
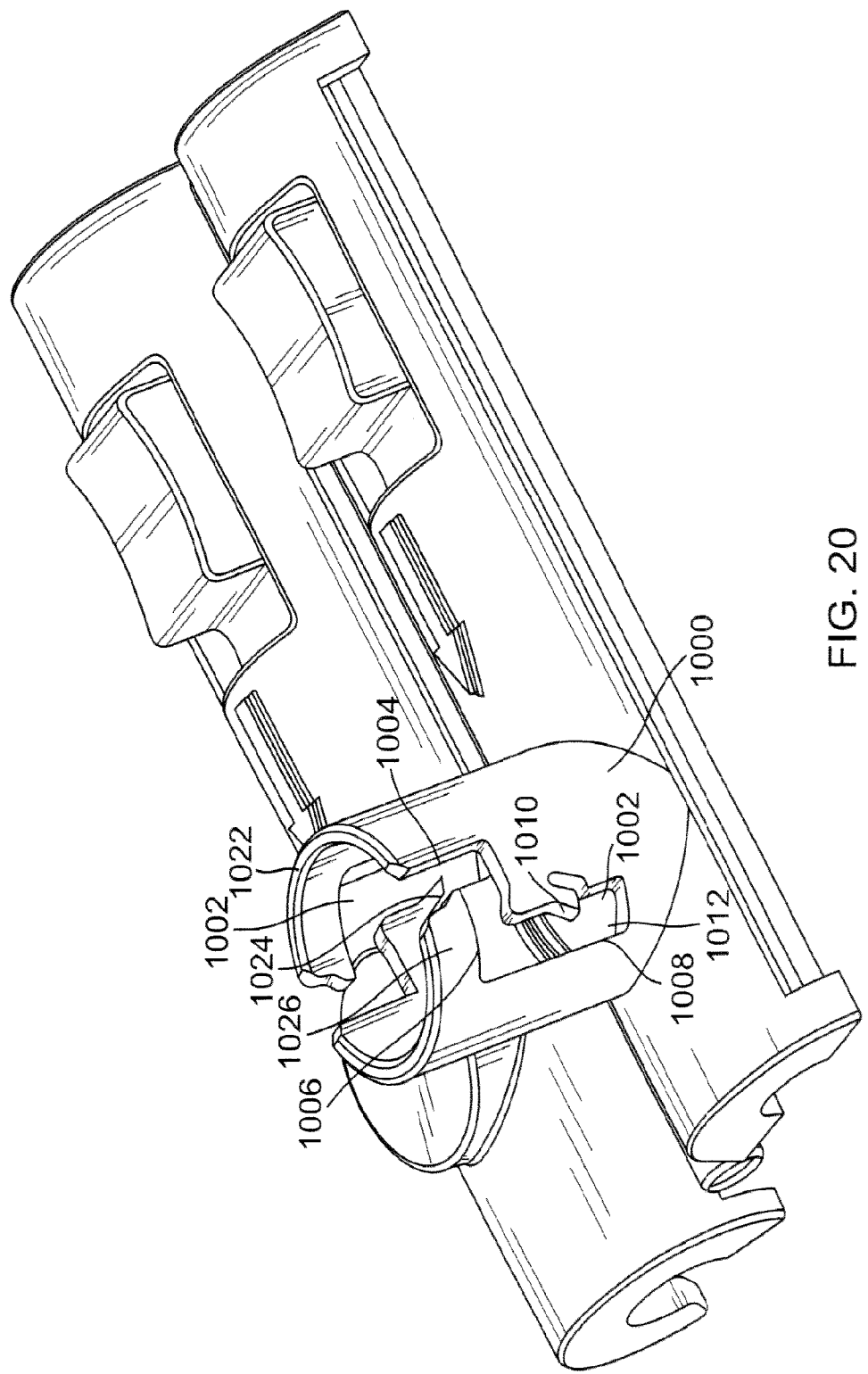
FIG. 20 is a front perspective view of a portion of another embodiment of the present apparatus for selectively establishing a needleless injection port on an IV tubing.
Figure 21:
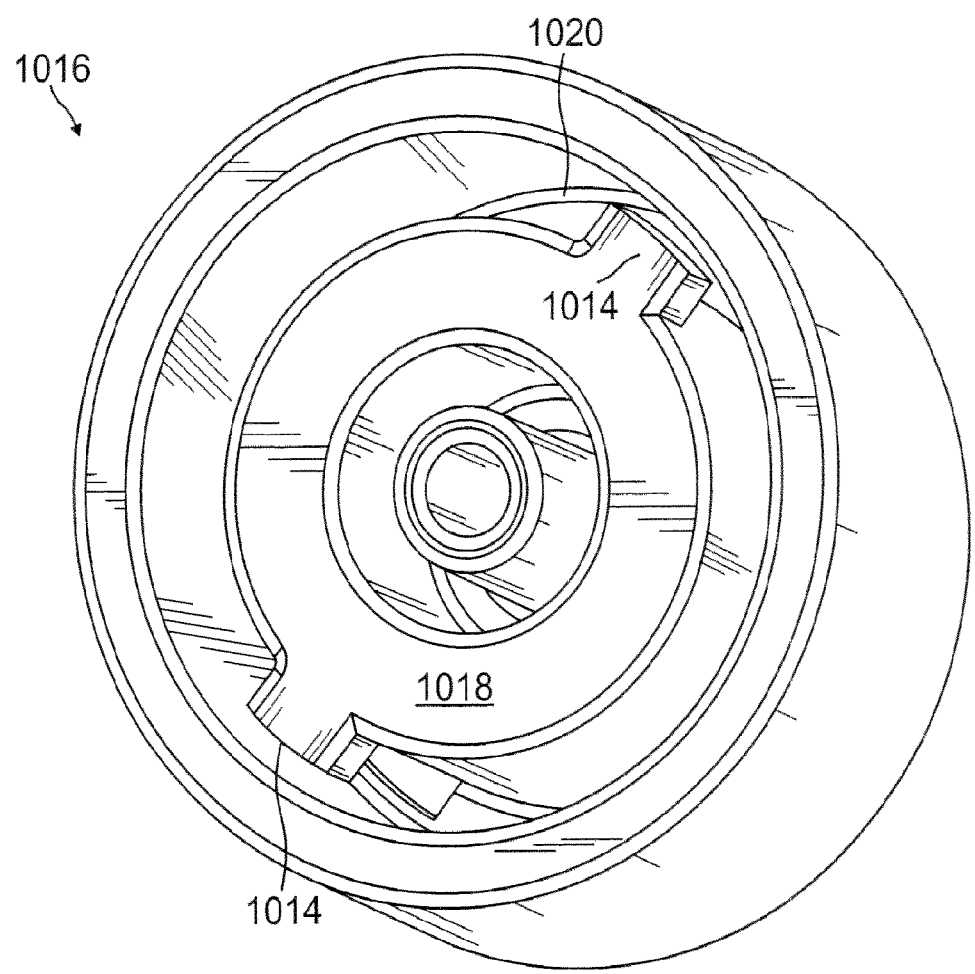
FIG. 21 is a front perspective view of a piston portion configured for use with the portion of FIG. 20.

FIGS. 20 and 21 illustrate another alternative embodiment of the present apparatus for selectively establishing a needleless injection port on IV tubing. With reference to FIG. 20, the apparatus includes a branch portion 1000 having guide channels 1002 in its sidewall. The illustrated embodiment includes two opposed guide channels 1002, but those of ordinary skill in the art will appreciate that the branch portion 1000 may include any number of guide channels 1002.

Each guide channel 1002 includes a proximal portion 1004 that extends longitudinally, a medial portion 1006 that extends circumferentially, and a distal portion 1008 that extends longitudinally. A cantilevered arm 1010, similar in structure and function to the cantilevered arms 544 described above with respect to FIG. 12, extends into the distal portion 1008 of the guide channel 1002. A space 1012 distal of the cantilevered arm 1010 traps a tab 1014 on the piston portion 1016 (FIG. 21), as described in detail below.

With reference to FIG. 21, the piston portion 1016 includes first and second tabs 1014. The tabs 1014 extend outwardly from an annularly shaped intermediate shaft portion 1018 into an annular space 1020. To mount the piston portion 1016 on the branch portion 1000, the proximal end 1022 of the branch portion 1000 is positioned within the annular space 1020 such that the tabs 1014 are aligned with the proximal portions 1004 of the guide channels 1002. A tab 1024 extends into each proximal portion 1004, narrowing the width of proximal portion 1004 in that region. To advance the tabs 1014 past the tabs 1024, force must be applied to squeeze the tabs 1014 through the narrower width in the region of the tabs 1024. The proximal wall 1026 of the branch portion 1000 flexes outwardly to allow the tabs 1024 to pass, and then snaps back to secure the tabs 1024 beneath the tabs 1014 and secure the piston portion 1016 on the branch portion 1000.

To advance the piston portion 1016 distally with respect to the branch portion 1000, the operator rotates the piston portion 1016 such that the tabs 1024 advance through the medial portion 1006 toward the distal portion 1008. A tab 1028 extends into the medial portion 1006 at the elbow between the medial portion 1006 and the distal portion 1008. The tab 1028 narrows the width of medial portion 1006 in that region. To advance the tabs 1014 past the tabs 1028, force must be applied to squeeze the tabs 1014 through the narrower width in the region of the tabs 1028. When the tabs 1014 advance past the tabs 1028 and into the distal portion 1008, the operator applies a distally directed force to the piston portion 1016. The tabs 1014 advance distally through distal portion 1008 as the piston portion 1016 advances distally along the branch portion 1000. The cantilevered arms 1010 trap the tabs 1014 in the space 1012 in a manner similar to that described above with respect to FIG. 12.

The present embodiments advantageously reduce the overall cost of IV tubing and needleless injection ports by decoupling the manufacturing processes for tubing and ports. Instead of manufacturing tubing with a built-in port, the present embodiments enable tubing and ports to be manufactured separately, and combined as needed by medical personnel. Fewer ports thus go unused.

The above description presents the best mode contemplated for carrying out the present apparatus for selectively establishing a needleless injection port on IV tubing, and associated methods, and of the manner and process of making and using it, in such full, clear, concise, and exact terms as to enable any person skilled in the art to which it pertains to make and use this apparatus. This apparatus is, however, susceptible to modifications and alternate constructions from that discussed above that are fully equivalent. Consequently, this apparatus is not limited to the particular embodiments disclosed and certain features disclosed for one embodiment may be incorporated in another embodiment provided their functions are compatible. On the contrary, this apparatus covers all modifications and alternate constructions coming within the spirit and scope of the apparatus as generally expressed by the following claims, which particularly point out and distinctly claim the subject matter of the apparatus. Further, the invention illustratively disclosed herein suitably may be practiced in the absence of any element, which his not specifically disclosed herein.

What is claimed is:

1. Apparatus configured to be secured to intravenous (IV) tubing to establish a needleless injection/aspiration port on the IV tubing, the apparatus comprising:
   an IV tubing-engaging portion having an internal surface configured to snugly engage an external surface of the IV tubing;
   a tubular branch portion extending from the IV tubing-engaging portion, the branch portion including a lumen;
   a first elastomeric sealing member located at a junction of the IV tubing-engaging portion and the branch portion, the sealing member fluidly isolating the lumen of the branch portion from an interior of the IV tubing-engaging portion;
   a compressible piston portion engaging the branch portion, a central shaft of the piston portion disposed at least partially within the lumen of the branch portion, the central shaft including a lumen;
   a puncturing member extending distally from the central shaft and including a lumen and a pointed distal tip;
   a valve member engaging a proximal end of the piston portion, the piston portion including a second elastomeric sealing member that provides selective sealing of a proximal end of the piston portion;
   a stabilizer extending proximally from an exterior surface of the IV tubing-engaging portion, the stabilizer engaging an exterior of the piston portion to support the piston portion during rotation relative to the branch portion; and
   wherein relative translation of the piston portion with respect to the branch portion in a first direction drives the pointed tip of the puncturing member through the first elastomeric sealing member and through a sidewall of the IV tubing to establish fluid communication between an interior of the IV tubing and the lumen in the puncturing member.

2. The apparatus of claim 1, wherein the stabilizer comprises first and second uprights located on opposite sides of the piston portion.

3. The apparatus of claim 1, wherein the stabilizer and the piston portion include overlapping flanges that resist axial movement of the piston portion proximally with respect to the stabilizer.

4. Apparatus configured to be secured to intravenous (IV) tubing to establish a needleless injection/aspiration port on the IV tubing, the apparatus comprising:
   an IV tubing-engaging portion having an internal surface configured to snugly engage an external surface of the IV tubing;
   a tubular branch portion extending from the IV tubing-engaging portion, the branch portion including a lumen;
   a first elastomeric sealing member located at a junction of the IV tubing-engaging portion and the branch portion, the sealing member fluidly isolating the lumen of the branch portion from an interior of the IV tubing-engaging portion;
   a compressible piston portion engaging the branch portion, a central shaft of the piston portion disposed at least partially within the lumen of the branch portion, the central shaft including a lumen;
   a puncturing member extending distally from the central shaft and including a lumen and a pointed distal tip;
   a valve member engaging a proximal end of the piston portion, the piston portion including a second elastomeric sealing member that provides selective sealing of a proximal end of the piston portion;
   wherein relative translation of the piston portion with respect to the branch portion in a first direction drives the pointed tip of the puncturing member through the first elastomeric sealing member and through a sidewall of the IV tubing to establish fluid communication between an interior of the IV tubing and the lumen in the puncturing member; and
   wherein the IV tubing-engaging portion further comprises a clamp configured to pinch the IV tubing to restrict fluid flow therethrough.

5. A method of securing apparatus to intravenous (IV) tubing to create a needleless injection/aspiration port on the IV tubing, the method comprising:
   positioning a first section of an IV tubing-engaging portion of the apparatus on the IV tubing;
   moving a second section of the IV tubing-engaging portion relative to the first section to at least partially surround a length of the IV tubing and to bring an internal surface of the IV tubing-engaging portion into snug engagement with an external surface of the IV tubing;
   engaging an injection apparatus with a valve member of the apparatus such that a male portion of the injection apparatus penetrates a slit in a first elastomeric sealing member of the valve member to open fluid communication through the valve member;
   translating the valve member and a piston portion to which the valve member is secured in a first direction relative to a tubular branch portion extending perpendicularly to the IV tubing-engaging portion;
   advancing the piston portion toward the IV tubing as the piston portion translates relative to the branch portion;
   advancing a puncturing member that extends distally from the piston portion toward the IV tubing as the piston portion advances toward the IV tubing;
   puncturing a second elastomeric sealing member located at a junction of the IV tubing-engaging portion and the branch portion with the puncturing member as it advances toward the IV tubing; and
   puncturing the IV tubing with the puncturing member to establish fluid communication between an interior of the IV tubing and a lumen in the puncturing member; and
   clamping the IV tubing to restrict fluid flow therethrough from a point upstream of the puncturing member.

6. The method of claim 5, wherein bringing the internal surface of the IV tubing-engaging portion into snug engagement with the external surface of the IV tubing establishes a seal at an interface between the internal surface and the IV tubing.

7. The method of claim 5, wherein engaging the injection apparatus with the valve member includes engaging a first Luer fitting on the injection apparatus with a second Luer fitting on the valve member and rotating the injection apparatus relative to the valve member.

8. The method of claim 5, wherein advancing the piston portion toward the IV tubing comprises advancing a central shaft of the piston portion into a lumen of the branch portion.

9. The method of claim 5, wherein as the puncturing member advances through the second elastomeric sealing member the second elastomeric sealing member creates a seal at an interface between the puncturing member and the second elastomeric sealing member.

10. The method of claim 5, further comprising latching the first and second sections of the IV tubing-engaging portion to one another to resist removal of the apparatus from the IV tubing.

11. The method of claim 5, further comprising injecting a fluid from the injection apparatus through the valve member and into the IV tubing.

12. The method of claim 5, further comprising disengaging the injection apparatus from the valve member to reestablish a seal at the slit in the first elastomeric sealing member.

* * * * *